(12) United States Patent
Gill et al.

(10) Patent No.: US 8,926,683 B2
(45) Date of Patent: Jan. 6, 2015

(54) STENT DELIVERY SYSTEMS AND METHODS

(75) Inventors: Darla Gill, Salt Lake City, UT (US); Rich Snider, Dallas, TX (US); Zeke Eller, Dallas, TX (US); Jim Mottola, Salt Lake City, UT (US); Tom Robinson, Addison, TX (US); Brenda Lyons, Loveland, OH (US)

(73) Assignee: Merit Medical Systems, Inc., South Jordan, UT (US)

( * ) Notice: Subject to any disclaimer, the term of this patent is extended or adjusted under 35 U.S.C. 154(b) by 482 days.

(21) Appl. No.: 13/313,929

(22) Filed: Dec. 7, 2011

(65) Prior Publication Data
US 2012/0310320 A1 Dec. 6, 2012

Related U.S. Application Data

(60) Provisional application No. 61/420,687, filed on Dec. 7, 2010.

(51) Int. Cl.
| | | |
|---|---|---|
| *A61F 2/06* | (2013.01) | |
| *A61F 2/966* | (2013.01) | |
| *A61F 2/95* | (2013.01) | |

(52) U.S. Cl.
CPC ......... *A61F 2/966* (2013.01); *A61F 2002/9665* (2013.01); *A61F 2002/9517* (2013.01)
USPC ......................................... 623/1.11; 606/108

(58) Field of Classification Search
CPC ............ A61F 2/966; A61F 2002/9517; A61F 2002/9665
USPC .......................... 606/108, 200; 623/1.11, 2.11
See application file for complete search history.

(56) References Cited

U.S. PATENT DOCUMENTS

| | | | |
|---|---|---|---|
| 5,201,757 | A | 4/1993 | Heyn et al. |
| 5,759,186 | A | 6/1998 | Bachmann et al. |

(Continued)

FOREIGN PATENT DOCUMENTS

| | | |
|---|---|---|
| DE | 9209908 | 9/1992 |
| DE | 4323866 | 1/1994 |

(Continued)

OTHER PUBLICATIONS

PCT Notification of Transmittal of the International Search Report and Written Opinion dated Nov. 23, 2006 for PCT/US2006/018811.

(Continued)

*Primary Examiner* — Julian W Woo
*Assistant Examiner* — Lucas Paez
(74) *Attorney, Agent, or Firm* — Stoel Rives LLP

(57) ABSTRACT

Apparatus, systems, and methods are provided for deploying an implantable device, such as a stent, within a lumen of a body of a patient. The delivery device may include an inner member and an outer sheath surrounding a distal portion of the inner member and configured to retain the implantable device sheathed near the distal end of the outer sheath until deployment. The outer sheath is slidably moveable relative to the inner member such that proximal movement of the outer sheath relative to the inner member deploys the implantable device. A trigger assembly of the delivery device can include an internal connector coupled to the outer sheath, a plurality of triggers, and a floater coupling two of the triggers. The triggers are serially retracted to deploy the stent. A panchor secures the stent against proximal and distal movement relative to the inner member during deployment.

27 Claims, 16 Drawing Sheets

(56) References Cited

U.S. PATENT DOCUMENTS

| | | | |
|---|---|---|---|
| 5,824,041 A | 10/1998 | Lenker et al. | |
| 5,868,755 A | 2/1999 | Kanner et al. | |
| 5,954,729 A | 9/1999 | Bachmann et al. | |
| 6,143,021 A | 11/2000 | Staehle | |
| 6,162,231 A | 12/2000 | Mikus et al. | |
| 6,391,051 B2 | 5/2002 | Sullivan, III et al. | |
| 6,413,269 B1 | 7/2002 | Bui et al. | |
| 6,428,566 B1 | 8/2002 | Holt | |
| 6,514,261 B1 | 2/2003 | Randall et al. | |
| 6,629,981 B2 | 10/2003 | Bui et al. | |
| 6,669,719 B2 | 12/2003 | Wallace et al. | |
| 6,726,712 B1 | 4/2004 | Raeder-Devens et al. | |
| 6,866,669 B2 | 3/2005 | Buzzard et al. | |
| 7,309,350 B2 * | 12/2007 | Landreville et al. | 623/1.11 |
| 7,393,357 B2 * | 7/2008 | Stelter et al. | 623/1.11 |
| 7,731,654 B2 | 6/2010 | Mangiardi et al. | |
| 8,439,934 B2 * | 5/2013 | Satasiya et al. | 606/108 |
| 8,518,099 B2 * | 8/2013 | Chanduszko et al. | 623/1.11 |
| 8,535,366 B2 | 9/2013 | Mangiardi et al. | |
| 2002/0151967 A1 | 10/2002 | Mikus et al. | |
| 2002/0183827 A1 | 12/2002 | Derus et al. | |
| 2003/0050686 A1 | 3/2003 | Raeder-Devens et al. | |
| 2003/0167060 A1 | 9/2003 | Buzzard et al. | |
| 2004/0193243 A1 | 9/2004 | Mangiardi et al. | |
| 2004/0267281 A1 | 12/2004 | Harari et al. | |
| 2005/0090887 A1 | 4/2005 | Pryor | |
| 2005/0125050 A1 | 6/2005 | Carter et al. | |
| 2005/0149160 A1 | 7/2005 | McFerran | |
| 2005/0278010 A1 | 12/2005 | Richardson | |
| 2007/0043421 A1 | 2/2007 | Mangiardi et al. | |
| 2007/0100421 A1 | 5/2007 | Griffin | |
| 2007/0208350 A1 | 9/2007 | Gunderson | |
| 2007/0270932 A1 | 11/2007 | Headley et al. | |
| 2009/0099636 A1 | 4/2009 | Chanduszko et al. | |
| 2009/0118740 A1 | 5/2009 | Mangiardi et al. | |
| 2009/0192518 A1 | 7/2009 | Golden et al. | |
| 2010/0049295 A1 | 2/2010 | Satasiya et al. | |

FOREIGN PATENT DOCUMENTS

| | | |
|---|---|---|
| EP | 0364420 | 4/1990 |
| EP | 0872220 | 10/1998 |
| WO | WO96/31174 | 10/1996 |
| WO | WO00/78246 | 12/2000 |
| WO | WO02/087470 | 11/2002 |
| WO | WO03/090644 | 11/2003 |
| WO | WO2004/030571 | 4/2004 |
| WO | WO2005/070095 | 8/2005 |
| WO | WO2008/042266 | 4/2008 |
| WO | PCT/US2012/062603 | 10/2012 |

OTHER PUBLICATIONS

The Supplementary European Search Report for EP Application No. 05705271.4, dated May 4, 2007.
International Search Report and Written Opinion for PCT/US2009/052691 dated Oct. 29, 2009.
Office Action for U.S. Appl. No. 11/432,964 dated Jul. 9, 2009.
Office Action for U.S. Appl. No. 11/432,964 dated Dec. 7, 2009.
International Search Report and Written Opinion for PCT/US05/00515 dated Aug. 4, 2005.
Office Action for U.S. Appl. No. 10/585,430 dated Dec. 8, 2009.
Office Action for U.S. Appl. No. 10/585,430 dated Nov. 9, 2010.
Office Action for U.S. Appl. No. 10/585,430 dated Jun. 7, 2011.
Office Action dated Jan. 22, 2013 for U.S. Appl. No. 10/585,430.
Office Action dated Jan. 3, 2014 for U.S. Appl. No. 11/432,964.
Notice of Allowance dated Jun. 11, 2013 for U.S. Appl. No. 10/585,430.
Office Action dated Jul. 25, 2013 for U.S. Appl. No. 11/432,964.
Office Action dated Nov. 14, 2012 for U.S. Appl. No. 12/535,980.
International Publication and Search Report dated Feb. 25, 2012 for WO10021836.
International Publication and Search Report dated Aug. 4, 2005 for WO2005070095.
International Publication and Search Report dated Jun. 14, 2012 for WO2012078794.
U.S. Appl. No. 13/664,137, Oct. 30, 2012, Robinson.
U.S. Appl. No. 13/664,200, Oct. 30, 2012, Robinson.
U.S. Appl. No. 13/664,200, Oct 30, 2012, Robinson.
U.S. Appl. No. 13/664,234, Oct. 30, 2012, Robinson.
U.S. Appl. No. 13/664,267, Oct. 30, 2012, Robinson.
Restriction Requirement dated Mar. 6, 2012 for U.S. Appl. No. 12/535,980.
Office Action dated May 25, 2012 for U.S. Appl. No. 12/535,980.
Office Action dated Jan. 31, 2012 for U.S. Appl. No. 10/585,430.
Notice of Allowance dated Mar. 6, 2013 for U.S. Appl. No. 12/535,980.
International Search Report and Written Opinion dated Mar. 29, 2013 for PCT/US2012/062603.
Office Action for U.S. Appl. No. 10/585,430 dated Aug. 13, 2012.

* cited by examiner

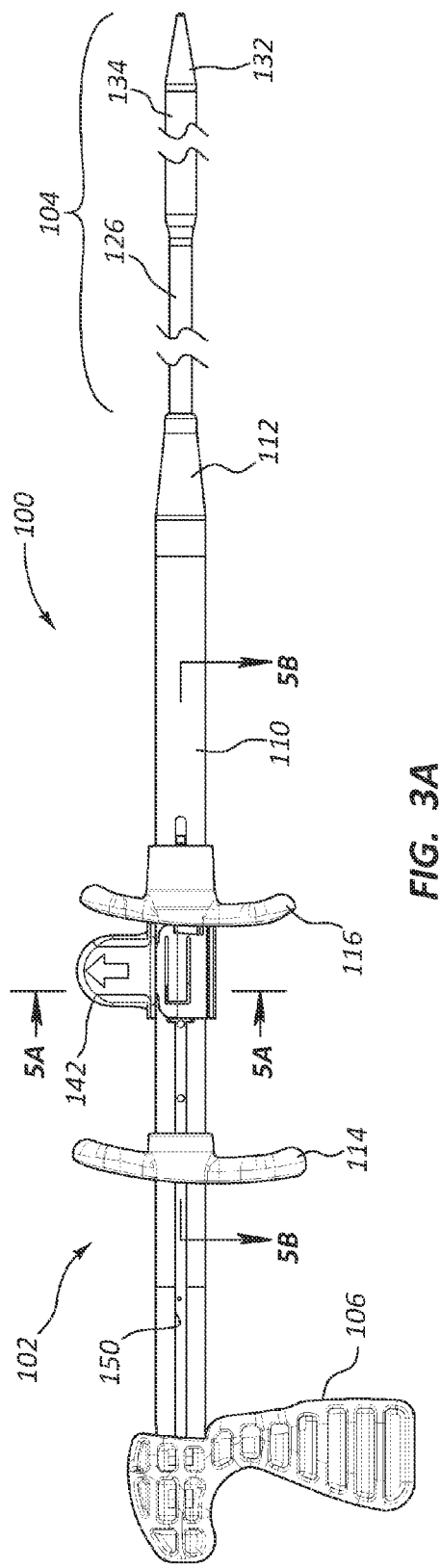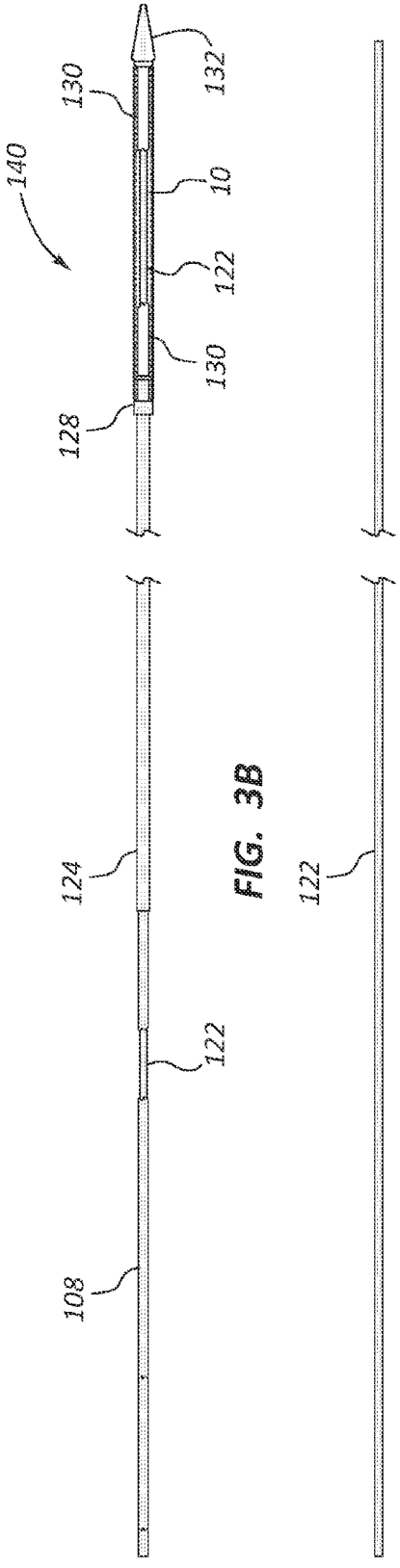
FIG. 3A
FIG. 3B
FIG. 3C

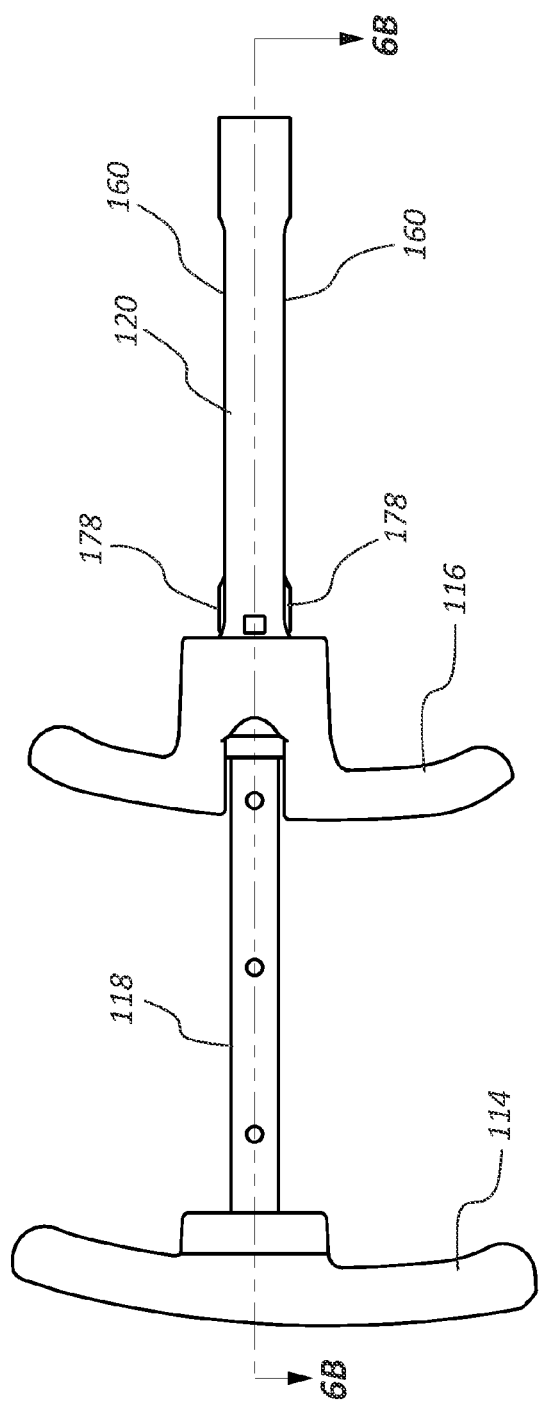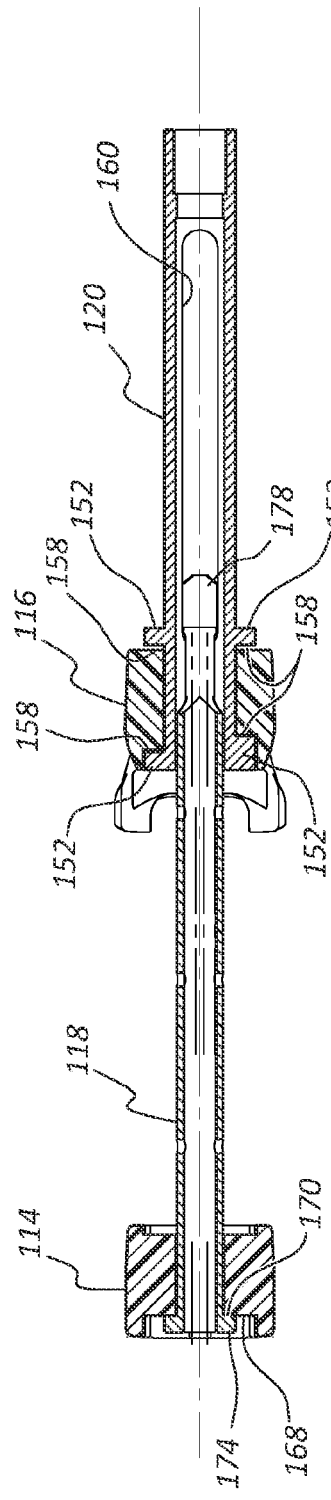
FIG. 6A
FIG. 6B

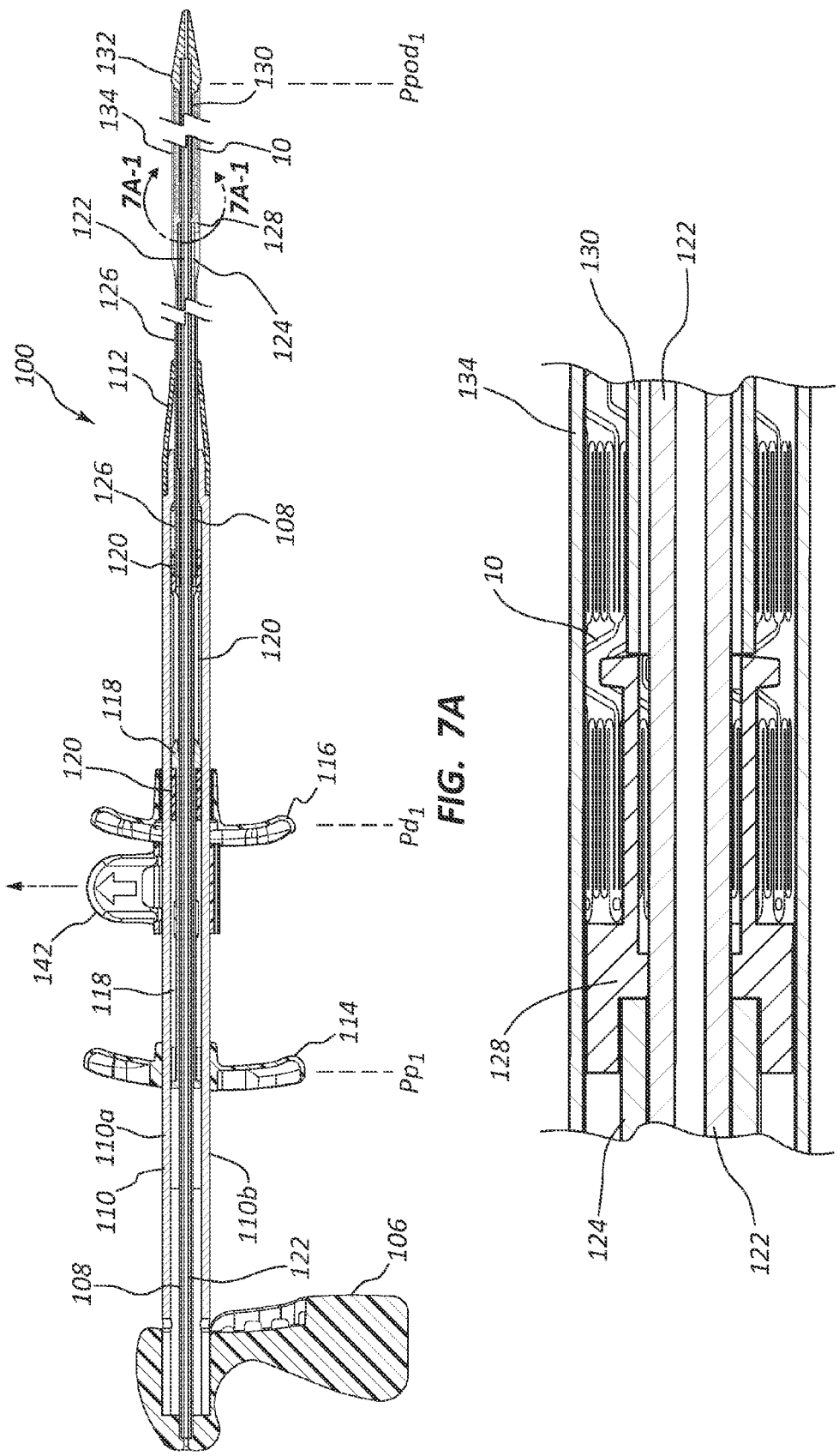

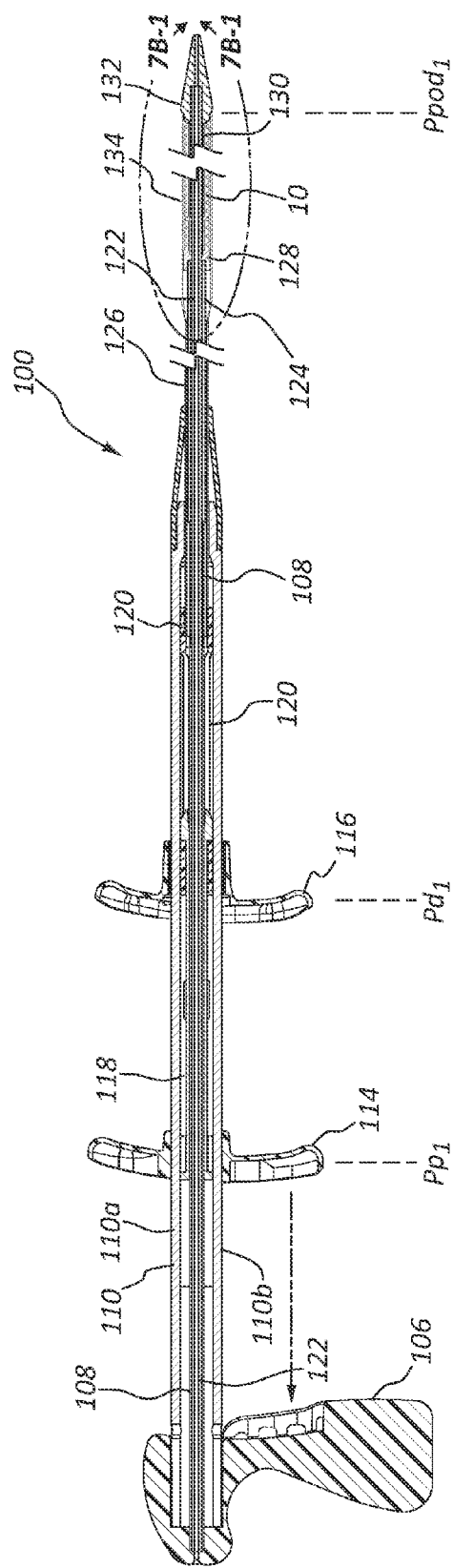

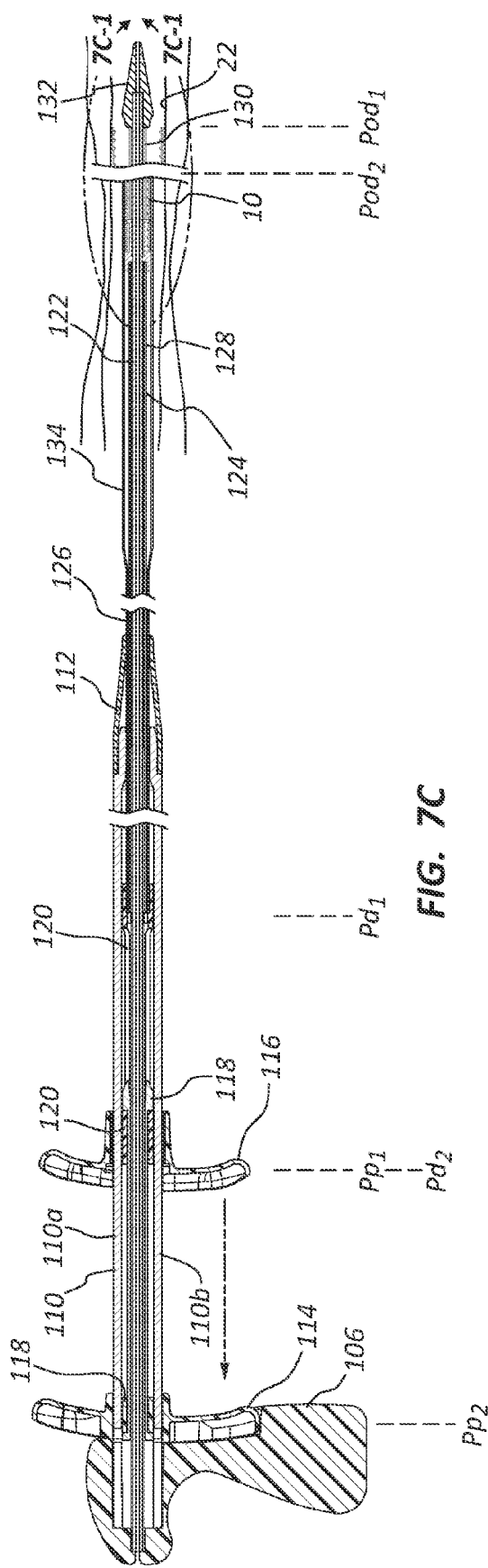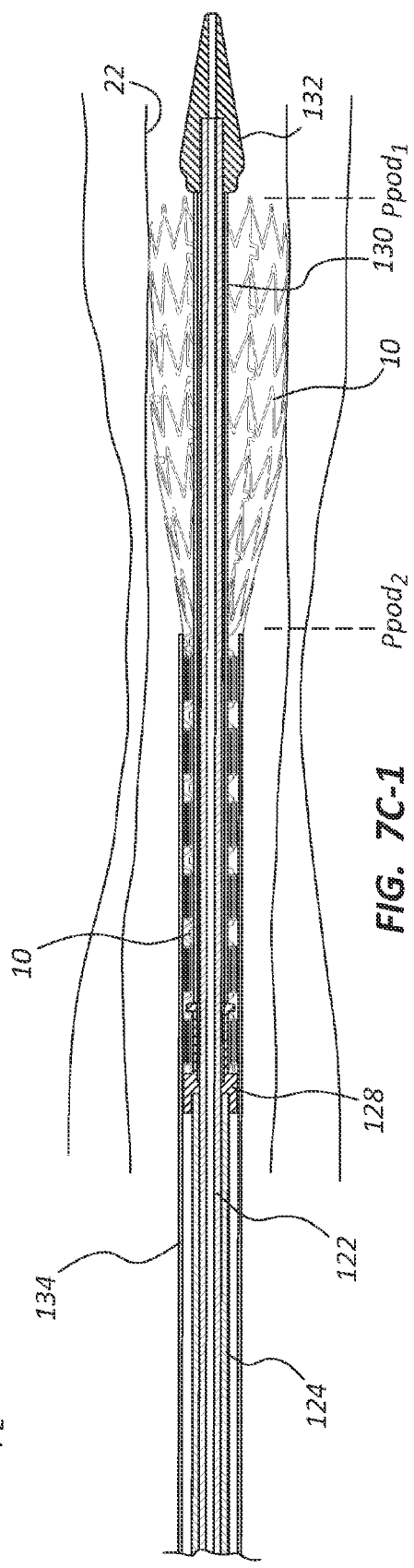
FIG. 7C
FIG. 7C-1

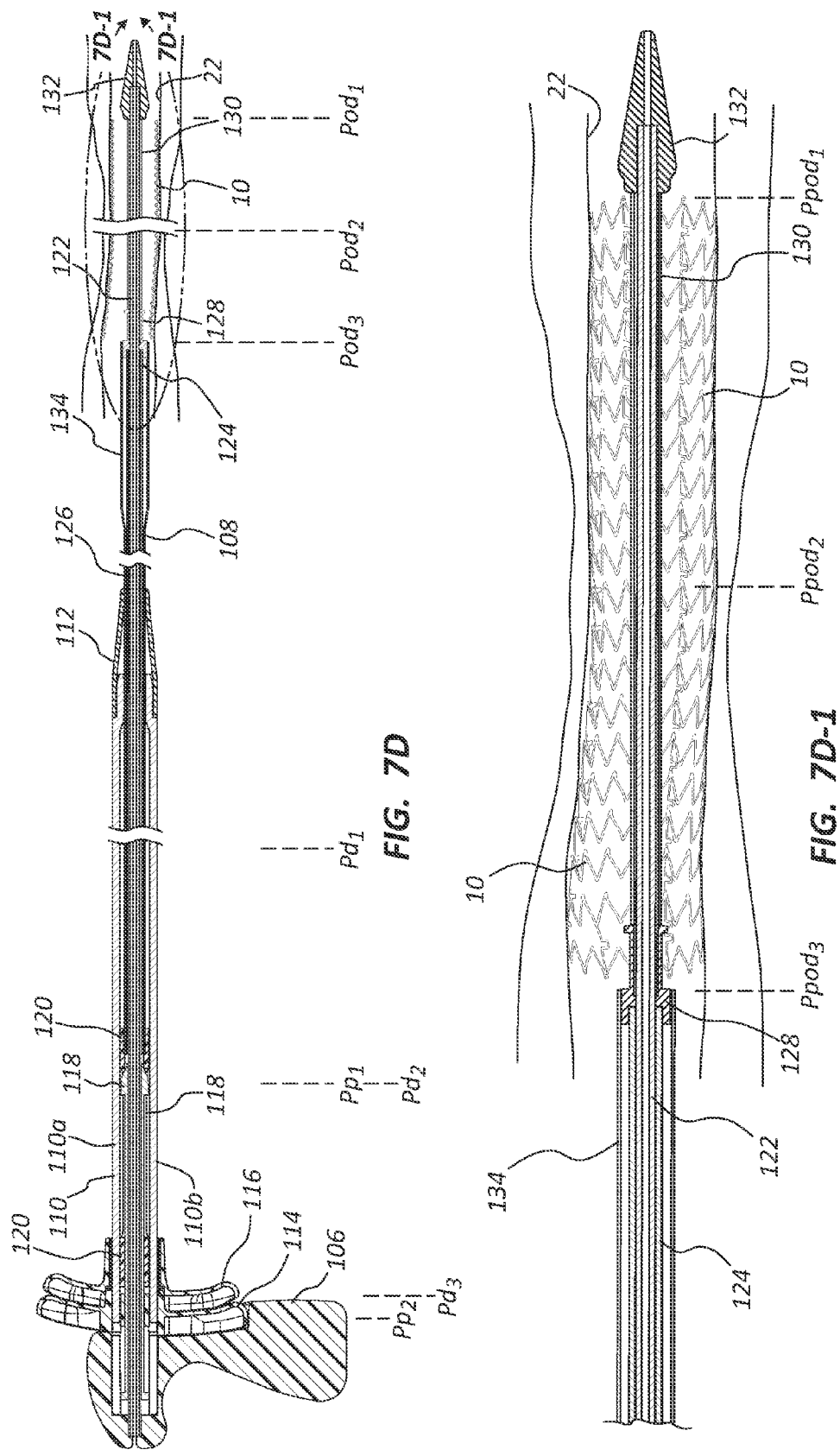

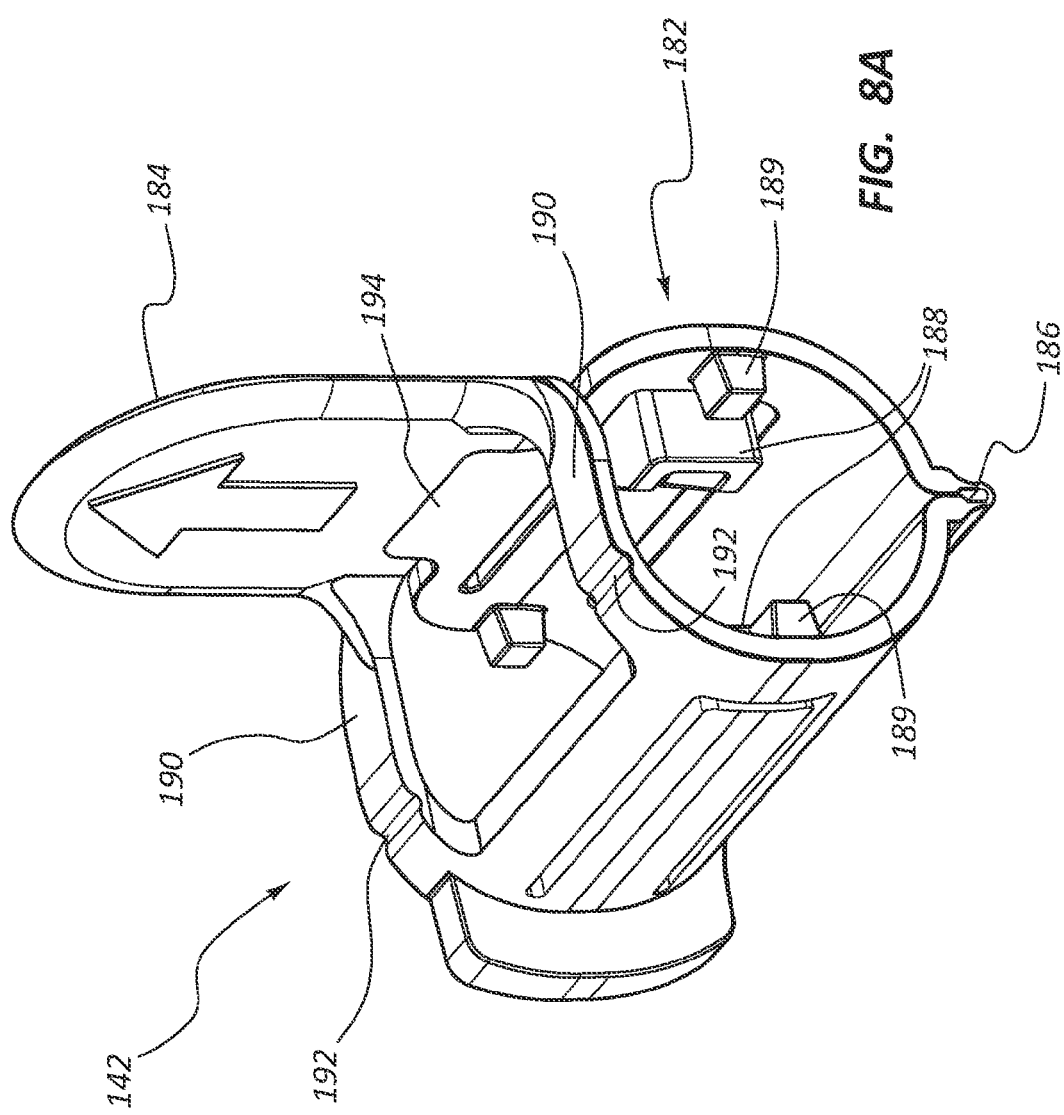

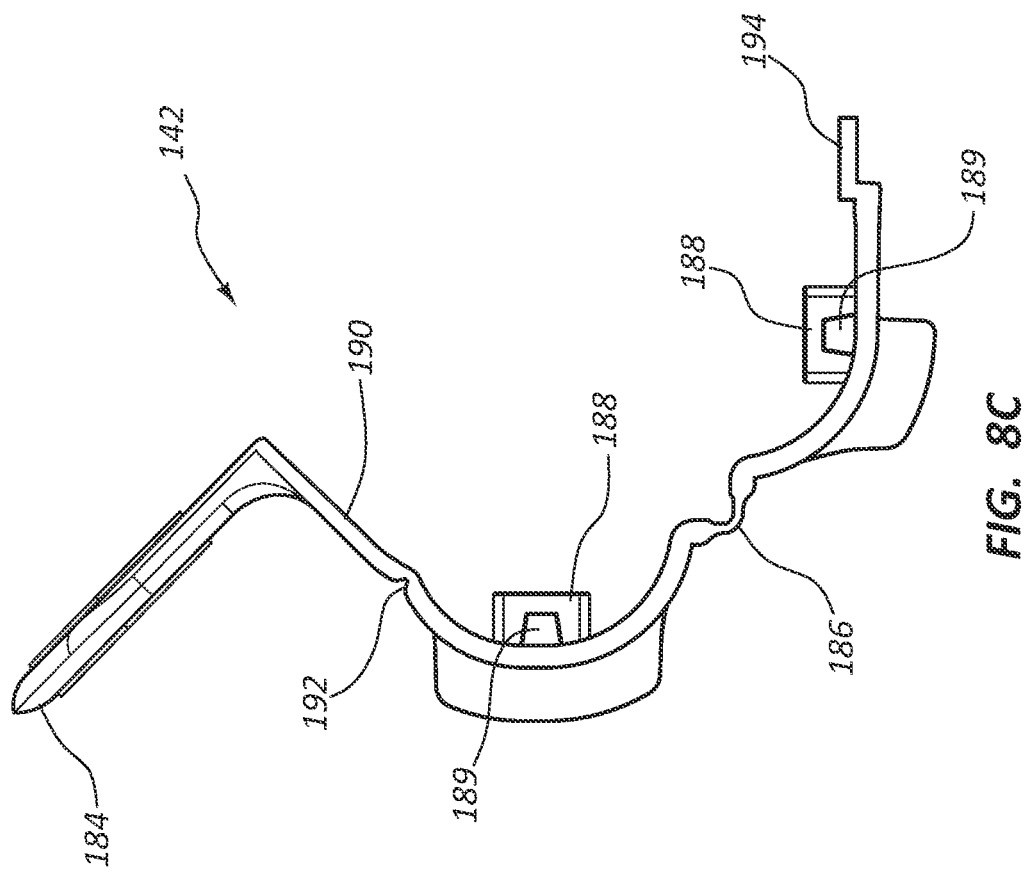
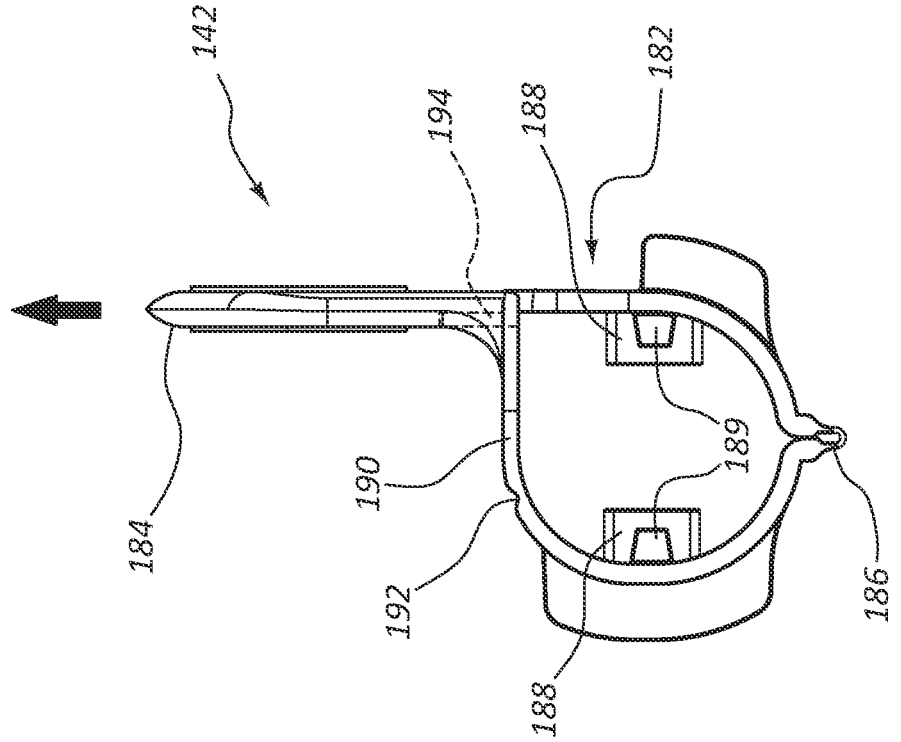
FIG. 8C
FIG. 8B

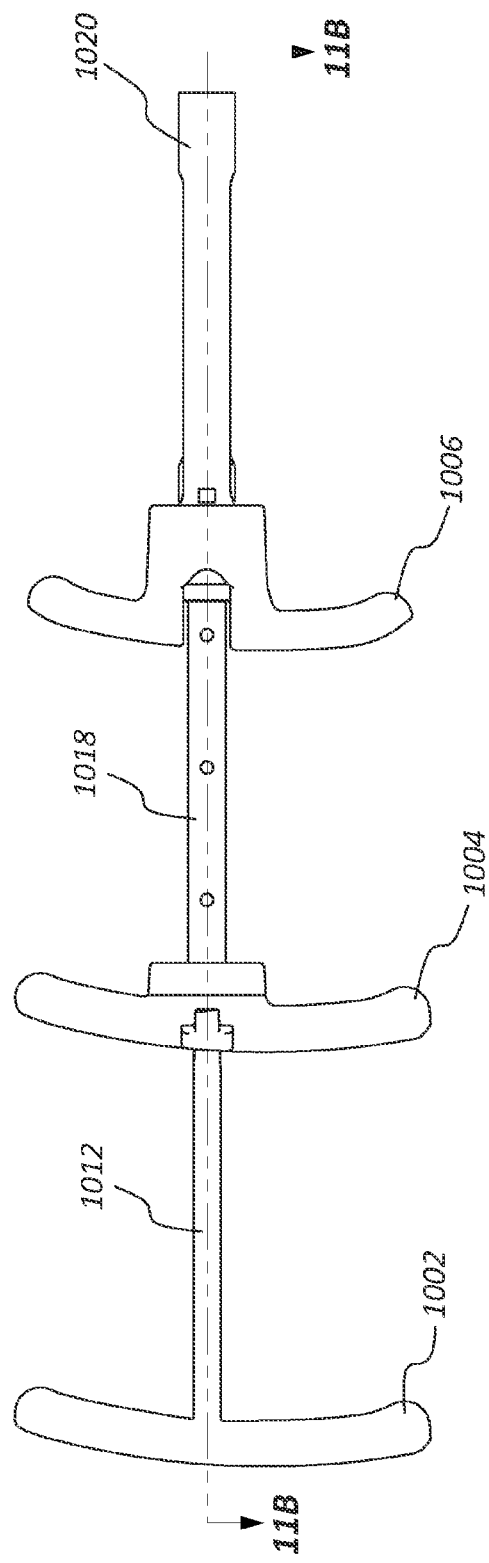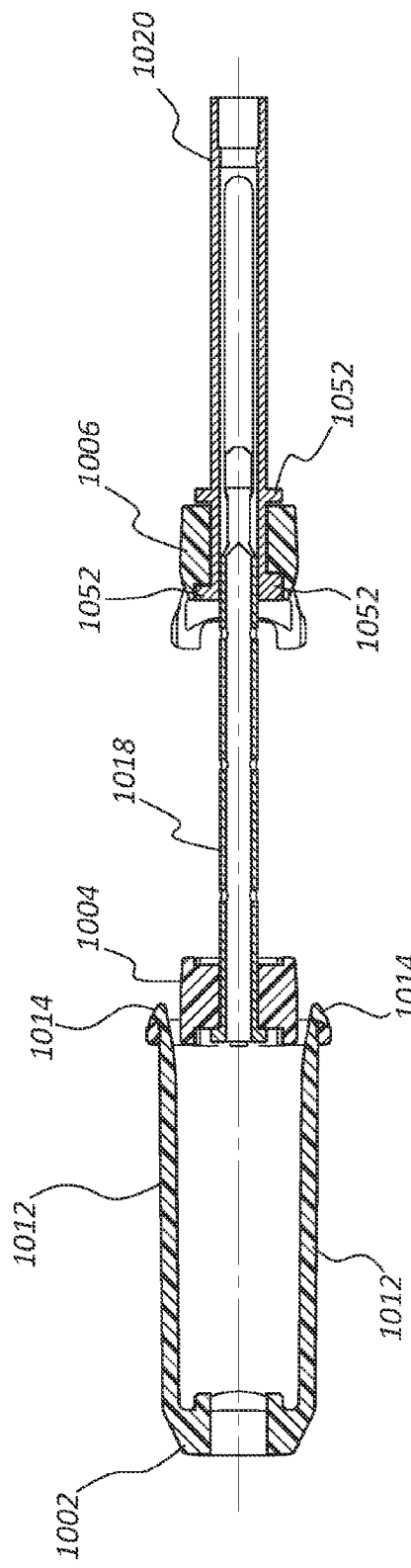
FIG. 11A
FIG. 11B

STENT DELIVERY SYSTEMS AND METHODS

RELATED APPLICATIONS

This application claims the benefit under 35 U.S.C. §119(e) of U.S. Provisional Patent Application No. 61/420,687, filed Dec. 7, 2010, and titled "STENT DELIVERY SYSTEM," which is hereby incorporated by reference herein its entirety.

TECHNICAL FIELD

The present disclosure relates generally to stent delivery devices.

BRIEF DESCRIPTION OF THE DRAWINGS

The written disclosure herein describes illustrative embodiments that are non-limiting and non-exhaustive. Reference is made to certain such illustrative embodiments that are depicted in the figures, in which:

FIGS. 3A-3C are partially exploded, cut-away, and/or cross-sectional side views of the stent delivery system of FIG. 1.

FIGS. 6A and 6B are side and top cross-sectional views, respectively, of an internal connector, a distal trigger, a floater, and a proximal trigger of the stent delivery system of FIG. 1, according to one embodiment of the present disclosure.

FIGS. 7A-7D are side longitudinal cross-sectional views of the trigger assembly of the stent delivery system of FIG. 1, at various positions during deployment of a stent.

FIGS. 8A-8C are a perspective view and end views of a trigger safety of a stent delivery system, according to one embodiment of the present disclosure.

FIGS. 11A and 11B are side and top cross-sectional views, respectively, of an internal connector, a distal trigger, a floater, and a proximal trigger of the stent delivery system of FIG. 10.

DETAILED DESCRIPTION

Figure 1:
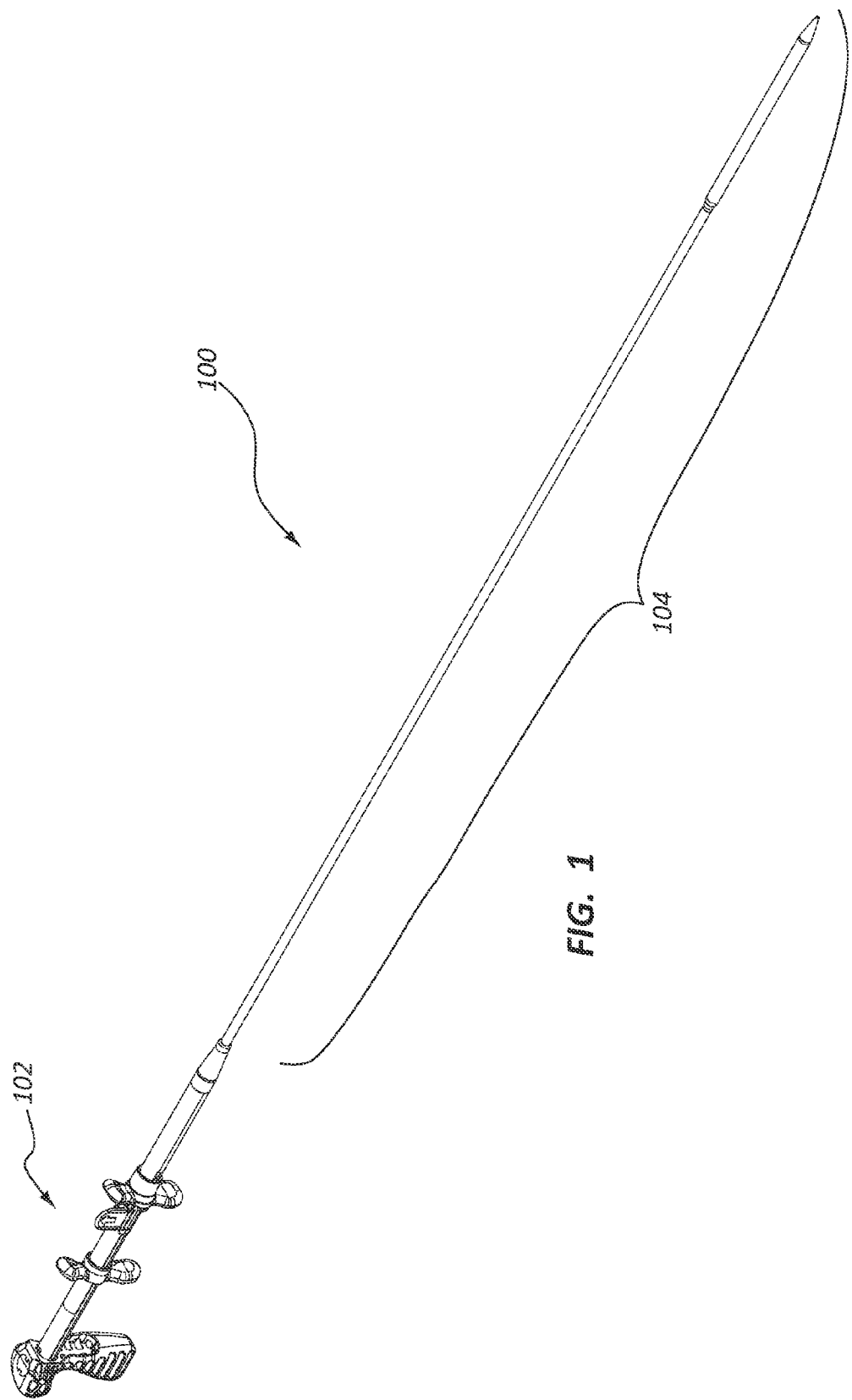
FIG. 1 is a perspective view of a stent delivery system, according to one embodiment of the present disclosure.

The present disclosure relates to a systems and methods for deploying an implantable device within a lumen.

Implantable medical devices are valuable tools of modern medicine. In general, an implantable device is a device or structure configured to be inserted or embedded into a patient for a variety of functions. Implantable devices include stents, filters, markers, drug delivery devices, valves, and monitors.

In particular, stents are implantable devices that are inserted into body lumina, such as vessels or passages, to keep the lumen open and prevent closure due to a stricture, external compression, or internal obstruction. Stents are commonly used to keep blood vessels open in the coronary arteries, and they are frequently inserted into the ureters to maintain drainage from the kidneys, the bile duct for pancreatic cancer or cholangiocarcinoma, or the esophagus or airways for strictures or cancer.

In order to serve its desired function, the stent and most other implantable devices must be delivered precisely and oriented correctly. Improper installation can lead to several adverse complications including tissue luminal inflammation and tissue granulation. In order to facilitate the delivery of implantable devices, delivery devices, such as endoscopes and catheters, have been utilized to deploy implantable devices more precisely.

Delivery devices vary in shape and structure. In general, a delivery device may include a handle and one or more movable tubular members extending from the handle. The delivery device may further include a deployment mechanism for moving or operating the tubular members between positions. The one or more moveable tubular members typically include an inner tubular member disposed within an outer tubular member. The outer tubular member is typically shorter than the inner tubular member and movable relative to the inner tubular member. A distal region of the outer tubular member generally surrounds the implantable device, such as a stent, and maintains the stent in a crimped or sheathed delivery configuration, while a distal region of the inner tubular member is surrounded by the stent. Once the sheathed stent is properly positioned at a targeted site, the outer tubular member may be retracted to deploy the stent and allow the stent to radially expand.

Because delivery devices are commonly designed to facilitate easy deployment, inadvertent or accidental deployment may easily occur. Safety mechanisms to secure the outer tubular member relative to the inner tubular member typically comprise a pin passing through both the outer tubular member and the inner tubular member. These "pin-type" safety mechanisms can be difficult to operate or even ineffective in some instances.

The present disclosure is directed to delivery systems, such as stent delivery devices, addressing various shortcomings of presently available stent delivery devices. In particular, the present disclosure provides a stent delivery system having a plurality of triggers and a trigger safety to prevent accidental or inadvertent deployment. A stent delivery system according to the present disclosure may also have an anchor/pusher ("panchor") component configured to engage the proximal end of a sheathed stent to restrict movement of the stent both proximally and distally.

The stents that may be delivered by the embodiments of stent delivery systems disclosed herein may include a support or scaffolding structure formed of a plurality of rows of struts or legs oriented about an outer circumference of the stent and connected by a plurality of connectors extending longitudinally with a longitudinal axis of the stent. For example, embodiments of such stents are disclosed in U.S. patent application Ser. No. 13/153,150, entitled "ESOPHOGEAL STENT," which is hereby incorporated by reference herein in its entirety. Additionally, the stents may comprise a variety of components, and the parameters of these components—such as shape, length, thickness, position, etc.—may greatly vary to provide a stent with certain properties.

Although described in terms of delivering a stent, a person having ordinary skill in the art will readily appreciate that the disclosed delivery systems can be used to deliver a variety of implantable devices, including but not limited to stents, filters, markers, drug delivery devices, valves, and monitors. In one embodiment, the present disclosure provides an esophageal stent delivery system.

The embodiments of the disclosure will be best understood by reference to the drawings, wherein like parts are designated by like numerals throughout. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

In some cases, well-known features, structures or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

FIG. 1 is a perspective view of a stent delivery system 100, according to one embodiment of the present disclosure. The stent delivery system 100 may comprise a trigger assembly 102 and a tubular member 104. The tubular member 104 is configured to house a sheathed stent. The trigger assembly 102 allows a practitioner to deploy the stent.

Figure 2:
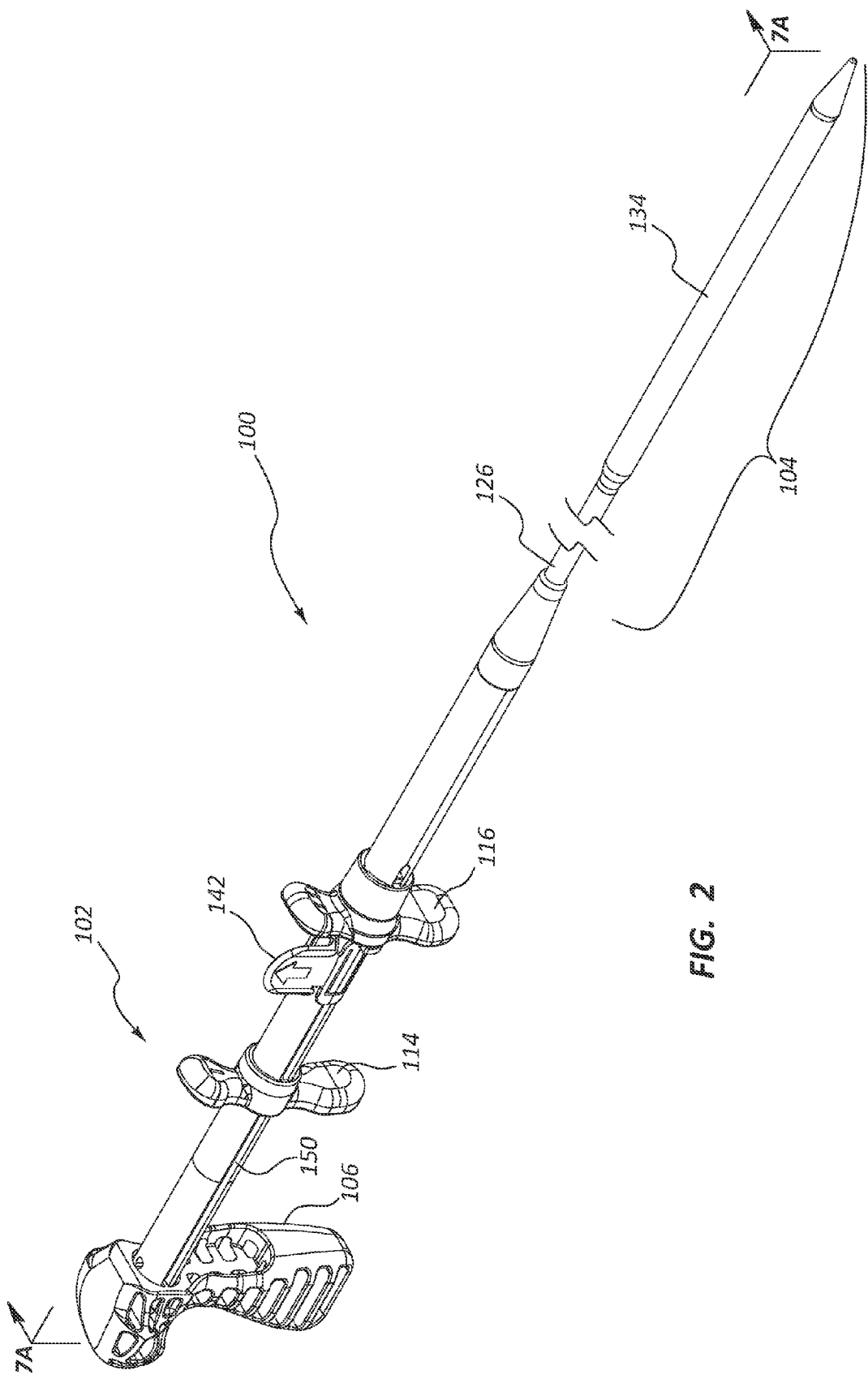
FIG. 2 is a closer perspective view of the stent delivery system of FIG. 1.

FIG. 2 provides a closer perspective view of the stent delivery system 100. The tubular member 104 may include an outer sheath 126 coupled to the trigger assembly 102. The outer sheath 126 may include a pod 134 at the distal end to enclose or sheathe a stent. The trigger assembly 102 may include a plurality of triggers 114, 116 that a practitioner can manipulate to retract the outer sheath 126 to deploy the stent. A proximal trigger 114 may be pulled proximally, toward a handle 106, to partially deploy the stent. A distal trigger 116 may then be pulled proximally, toward the handle 106 and the proximal trigger 114, to complete deployment of the stent. One or more trigger guide slots 150 and corresponding protrusions or trigger guides (not shown) may guide movement of the triggers 114, 116. A trigger safety 142 may inhibit operation of the trigger assembly 102 to restrict deployment of a sheathed stent. More specifically, the trigger safety 142 may limit proximal movement of the proximal trigger 114 and the distal trigger 116, thereby restricting deployment of the stent. In this manner, the trigger safety 142 may guard against inadvertent or accidental deployment of the stent.

Figure 4:
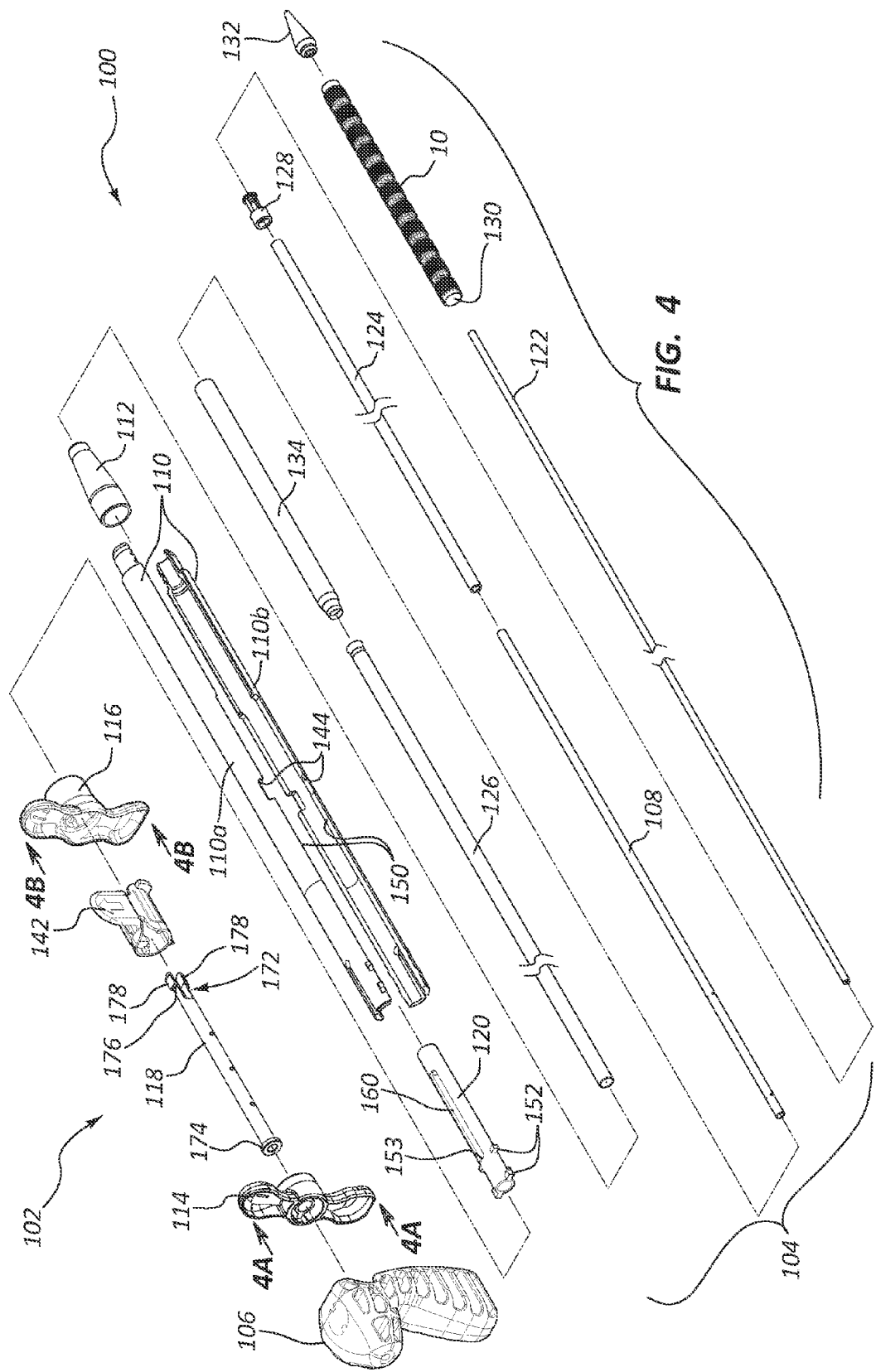
FIG. 4 is an exploded view of the stent delivery system of FIG. 1.

FIGS. 3A-3C are a partially exploded, cut-away, and/or cross-sectional side views of the stent delivery system 100 of FIG. 1. FIG. 4 is a fully exploded view of the stent delivery system 100. Referring collectively to FIGS. 3A-3C and 4, the illustrated stent delivery system 100 includes a handle 106, a rigid support tube 108, outer supports 110, a strain relief component 112, a proximal trigger 114, a distal trigger 116, a floater 118, an internal connector 120, an inner member 122, a middle sheath 124, an outer sheath 126, a pusher/anchor (hereinafter "panchor") 128, a spacer 130, and a tip 132. A pod 134 is configured to couple to the distal end of the outer sheath 126 to house a sheathed stent 10.

The trigger assembly 102, including the triggers 114, 116, the internal connector 120, and the floater 118, facilitates deployment of the stent 10 from a sheathed position within the pod 134. More specifically, the trigger assembly 102 facilitates moving the outer sheath 126 proximally relative to the inner member 122, thereby retracting the pod 134 from around the stent to expose and deploy the stent 10. Still more specifically, the internal connector 120 is bonded to the outer sheath 126 and proximal movement of the internal connector 120 relative to the handle 106 (and relative to the inner member 122 and outer supports 110) causes proximal movement of the outer sheath 126 relative to the inner member 122. Proximal movement of the outer sheath 126 relative to the inner member 122 results in deployment of a stent 10 sheathed within the pod 134. The triggers 114, 116 allow a practitioner to retract the outer sheath 126 proximally relative to the inner member 122 to deploy the stent, as will be explained in greater detail below with reference to FIGS. 7A-7D.

The handle 106 is configured to be easily grasped by a practitioner to secure and control the stent delivery system 100. In the illustrated embodiment, the handle 106 is shaped like the handle or butt of a handgun and configured to position the triggers 114, 116 similar to the positioning of the trigger of a handgun. The handle 106 may be ergonomically configured to be comfortably gripped in a practitioner's hand.

The inner member 122 may be an elongate tube that extends toward a distal end of the delivery system 100 from the handle 106, through the trigger assembly 102, through the tubular member 104, to the tip 132. The inner member 122 may be the inner-most component of the stent delivery system 100. The inner member 122 is configured to receive a guidewire (not shown) that can guide insertion of the tubular member 104 into a body lumen where the stent 10 is to be deployed. The inner member 122 may be formed of a flexible material, such as polyethylene, which can be easily manipulated over the guidewire and into a body lumen. In other embodiments, the inner member 122 may be formed of other flexible materials, including but not limited to nylon, Pebax, polypropylene, and Teflon. In still other embodiments, the inner member 122 may extend toward the distal end but not to the tip 132. In still other embodiments, the inner member 122 may comprise multiple parts, such that a distal portion of the inner member 122 may be couple to a proximal portion of the inner member 122 at a time prior to use of the delivery system 100 to deploy a stent 10.

An inner assembly 140 (FIG. 3B), which may include the rigid support tube 108, the middle sheath 124, the panchor 128, the spacer 130 and the tip 132, may be disposed coaxially around a portion or all of the inner member 122. The rigid support tube 108 may be securely fixed to the handle and may be configured to secure a proximal end of the inner member 122 to the handle 106. In the illustrated embodiment, the rigid support tube 108 may be formed of a metal, such as steel, and may be hollow and configured to receive the inner member 122. The steel rigid support tube 108 may then be crimped at one or more points to secure the inner member 122 inside. The rigid support tube 108 may provide a rigid internal structure to support the triggers 114, 116, the outer supports 110, and/or the trigger assembly 102. In another embodiment the rigid support tube 108 may be formed of a rigid material, such as plastic, and may be secured to the inner member 122 by bonding, gluing, or other manner of affixing or securing the inner member 122 within or to the rigid support tube 108.

The tip 132 is positioned at the distal end of the inner member 122. In the illustrated embodiment, the tip 132 is bonded to or otherwise connected to the inner member 122. The tip 132 may be formed of a molded plastic. The tip 132 may include a narrow lumen 133 that connects to the lumen of the inner member 122 to allow a guidewire to be inserted into the inner member 122. The tip 132 may be formed in a conical shape, tapering toward the distal end, to guide the tubular member 104 during insertion into a patient's body. The tip 132 may also be configured to protect the inner member 122 and/or the pod 134 from obstruction during shipping and prior to use of the stent delivery system 100.

The spacer 130 is positioned around the inner member 122 and extends proximally from the tip 132 to the panchor 128. The spacer 130 provides a surface about which the stent 10 can be compressed and sheathed within the pod 134. The panchor 128 is positioned adjacent the distal end of the inner member and also around the inner member 122 in abutment with the proximal end of the spacer 130. The panchor 128 is configured to secure the stent 10 within the pod 134. The panchor 128 restricts movement of the stent both proximally and distally relative to the panchor 128, as will be described below in greater detail with reference to FIG. 9.

The middle sheath 124 is positioned around the inner member 122 in abutment with the rigid support tube 108 and the panchor 128. The middle sheath 124 may function as a space-filler between the inner member 122 and the outer sheath 126. By filling the space between the inner member 122 and the outer sheath 126, the middle sheath can provide additional structural support for the inner member 122 against buckling, crimping, and other undesired bending and/or collapse of the inner member 122. In particular, pressure on the inner member 122 created by forces in the longitudinal direction of the inner member 122 during deployment of a stent can cause the inner member 122 to buckle, crimp, or otherwise bend in an undesirable fashion. The middle sheath 124 and the outer sheath 126 (which envelopes the middle sheath 124) provide additional structural support against buckling, crimping or other undesired bending of the inner member 122.

The inner assembly 140 may remain substantially fixed (in the proximal and distal directions) relative to the handle 106. The outer sheath 126 is retracted proximally over the inner assembly 140 to expose the distal portion of the inner assembly 140. The trigger assembly 102 facilitates proximal retraction of the outer sheath 126.

The outer sheath 126 substantially encases the inner assembly 140, or at least a distal portion of the inner assembly 140. In the illustrated embodiment, the outer sheath 126, in a fully extended configuration (i.e., completely undeployed) may abut the tip 132 and extend proximally to the proximal end of the middle sheath 124, where the outer sheath 126 couples to the internal connector 120. As can be appreciated, in other embodiments the outer sheath 126 may extend proximally to a greater or lesser degree as a function of the positioning of the and/or coupling to the internal connector 120 and/or distal trigger 116. The outer sheath 126 may be formed of a flexible material, such as Pebax, which can be manipulated into a body lumen of a patient. In other embodiments, the outer sheath 126 may be formed of other flexible materials, including but not limited to polyethylene, nylon, polypropylene, and Teflon.

The outer supports 110 support the trigger assembly 102. The outer supports 110 may include a plurality of elongate shafts secured to and/or extending from the handle 106. The outer supports 110 generally form a support structure for the plurality of triggers 114, 116. The outer supports 110 may be configured to provide a guide for a plurality of triggers 114, 116, a housing for the trigger assembly 102, and a structure against which the trigger safety 142 can secure the triggers 114, 116. In the illustrated embodiment, the outer supports 110 include an upper outer support 110a and a lower outer support 110b (collectively 110), each configured in a half cylindrical shape. The outer supports 110 may mate together to form a tubular shaped housing around a portion of the proximal end of the outer sheath 126, the internal connector 120, the floater 118, and a proximal portion of the inner assembly 140.

The triggers 114, 116 may be mounted on and/or positioned around the outside of the outer supports 110 and are slidably movable, proximally and/or distally relative to the outer supports 110. The outer supports 110 also may be configured to form or otherwise provide one or more trigger guide slots 150 to restrict rotational movement of the triggers about a longitudinal axis of the outer supports 110. The trigger guide slots 150 may also extend longitudinally along a length of the outer supports to provide a track or guide for the triggers 114, 116 as they move proximally and/or distally relative to the outer supports 110. A proximal end of the outer supports 110 couples to the handle 106 and a distal end of the outer supports couples to the strain relief component 112. The outer supports 110 may also provide one or more trigger safety notches 144 configured to be engaged by the trigger safety 142 to limit proximal movement of the distal trigger 116. In the illustrated embodiment, the trigger safety notches 144 are adjacent to the trigger guide slots 150.

The strain relief component 112 couples to the outer supports 110 and abuts against the outer sheath 126. The strain relief component 112 is molded of soft Pebax to provide flexibility. The strain relief component 112 may be configured to relieve strain on the outer sheath 126 as the tubular member 104 is manipulated during insertion into a patient's body. Specifically, the strain relief component 112 is configured to allow the outer sheath 126 to be displaced at an angle to the outer supports 110 without kinking the outer sheath 126. This translates to allowing the user to position the outer sheath 126 at an angle to a main axis of the handle 106 and triggers 114, 116 without kinking the outer sheath 126. If the outer sheath 126 is kinked, then the stent may not deploy. The strain relief component 112 guards against kinking of the outer sheath 126.

The internal connector 120 couples the outer sheath 126 and the distal trigger 116. The internal connector 120 may be a rigid elongate tubular structure. In the illustrated embodiment, one or more protrusions 152 on the internal connector 120 near the proximal end extend radially outward to engage the distal trigger 116. The internal connector 120 is positioned within the housing formed by the outer supports 110. A distal portion of the internal connector 120 is bonded to the outer sheath 126. Accordingly, proximal movement of the internal connector 120 causes proximal movement of the outer sheath 126 relative to the inner member 122. Proximal movement of the outer sheath 126 relative to the inner member 122 results in deployment of a stent 10 sheathed within the pod 134. In one embodiment the internal connector 120 may be partially inserted into a lumen of the outer sheath 126, such that an outer surface of the internal connector 120 is bonded to an interior surface of the outer sheath 126. In another embodiment, the outer sheath 126 may be received into the lumen of the internal connector 120, such that an interior surface of the internal connector 120 is bonded to an outer surface of the outer sheath 126. In still another embodiment, a distal edge of the internal connector 120 may be bonded to a proximal edge of the outer sheath 126.

The internal connector 120 may further include a floater engagement surface 153 configured to be engaged by the floater 118 as the floater 118 moves proximally relative to the internal connector 120, toward the handle of the delivery system. In the illustrated embodiment, the floater engagement surface is a proximal end of a floater engagement channel 160 in the internal connector. The internal connector 120 includes a pair of floater engagement channels 160 configured to receive and guide a pair of barbed prongs 176 of the floater 118. As the barbed prongs 176 move proximally within the floater engagement channels 160, barbs 178 on the barbed prongs 176 engage the floater engagement surface 153. Accordingly, proximal movement of the floater 118 results in proximal movement of the internal connector 120. As can be appreciated, the floater engagement surface 153 may also be positioned on the distal trigger 116, in another embodiment.

Figure 4B:
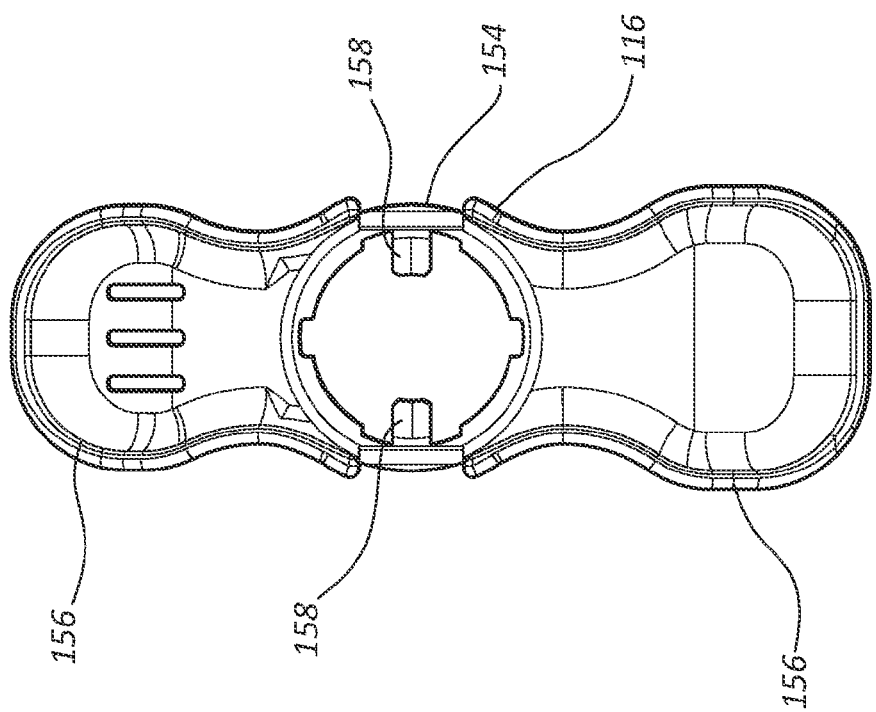
FIGS. 4A and 4B are end view of triggers of the stent delivery system of FIG. 1

The distal trigger 116 may include a ring-shaped base 154 with a pair of fingerholds 156 extending radially outward from the outer surface of the base 154 directly opposite one another. One or more trigger guides 158 (shown in FIG. 4B) may protrude radially inward from the base 154 to engage the trigger guide slot 150 formed by the outer supports 110. The trigger guides 158 may restrict rotation of the distal trigger 116 about the outer supports 110 while allowing proximal and distal movement of the distal trigger 116. The distal trigger 116 is configured to engage or otherwise couple to the internal connector 120.

Figure 4A:
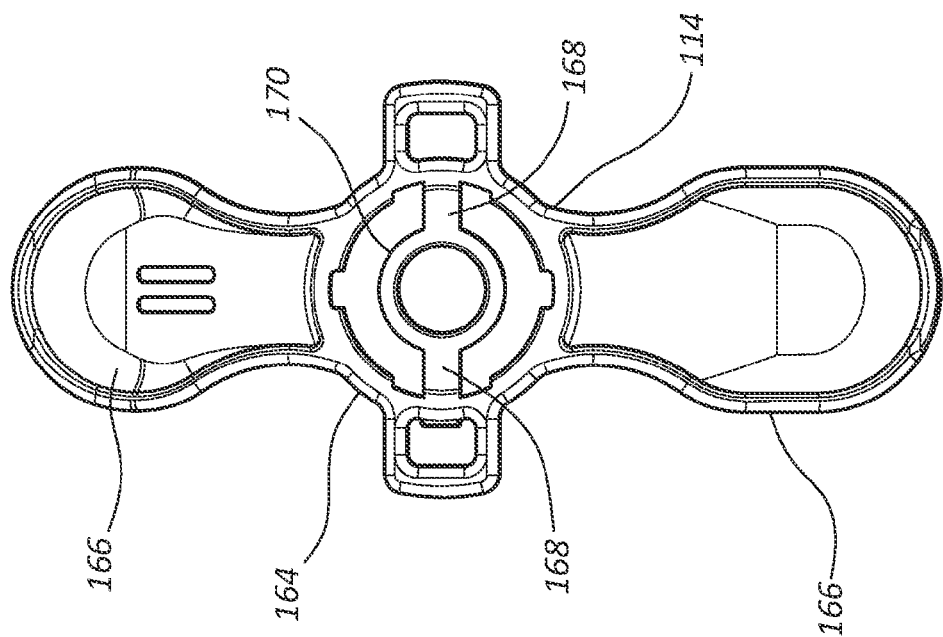

The proximal trigger 114 may be configured similar to the distal trigger, having a ring-shaped base 164 and a pair of fingerholds 166 extending radially outward from the outer surface of the base 164 directly opposite one another. One or more trigger guides 168 (shown in FIG. 4A) may protrude radially inward from the base 164 to engage the trigger guide slot 150 formed by the outer supports 110. The trigger guides 168 may restrict rotation of the proximal trigger 114 about the outer supports 110 while allowing proximal and distal movement of the proximal trigger 114.

The floater 118 may comprise a tubular shaft having a distal engagement mechanism 172 and a proximal engagement mechanism 174. In the illustrated embodiment, the distal engagement mechanism 172 may be one or more barbed prongs 176 at the distal end of the floater 118. The barbed prongs 176 may include outwardly protruding barbs 178. The barbs 178 may be configured to engage the distal trigger 116 and/or the proximal end of the internal connector 120 as the floater 118 is retracted proximally toward the handle 106. The barbs 178 may also be configured to allow the floater 118 to move distally and to telescope into the internal connector 120. Stated differently, the distal engagement mechanism 172 may allow the floater to move distally relative to the distal trigger 116 and the internal connector 120 (and telescope into the internal connector 120) and engages the internal connector 120 (at the proximal end) and/or the distal trigger 116 to limit movement of the of the floater 118 proximally relative to the internal connector 120 and/or the distal trigger 116. Described still another way, the distal engagement mechanism 172 may allow the distal trigger 116 and the internal connector 120 to move proximally relative to the floater 118, such that the distal trigger 116 can be retracted proximally toward the proximal trigger 114, as will be described in greater detail below.

In the illustrated embodiment, the proximal engagement mechanism 174 may include a flange or lip around the circumference of the floater 118 at the proximal end. The proximal engagement mechanism 174 may be configured to engage the floater engagement ring 170 (shown in FIG. 4A) of the proximal trigger 114, such that proximal movement of the proximal trigger 114 results in proximal movement of the floater 118. Accordingly, proximal movement of the proximal trigger 114 relative to the handle results in proximal movement of the floater 118, the distal trigger 116, the internal connector 120, and the outer sheath 126, thereby at least partially deploying the stent 10.

Figure 5A:
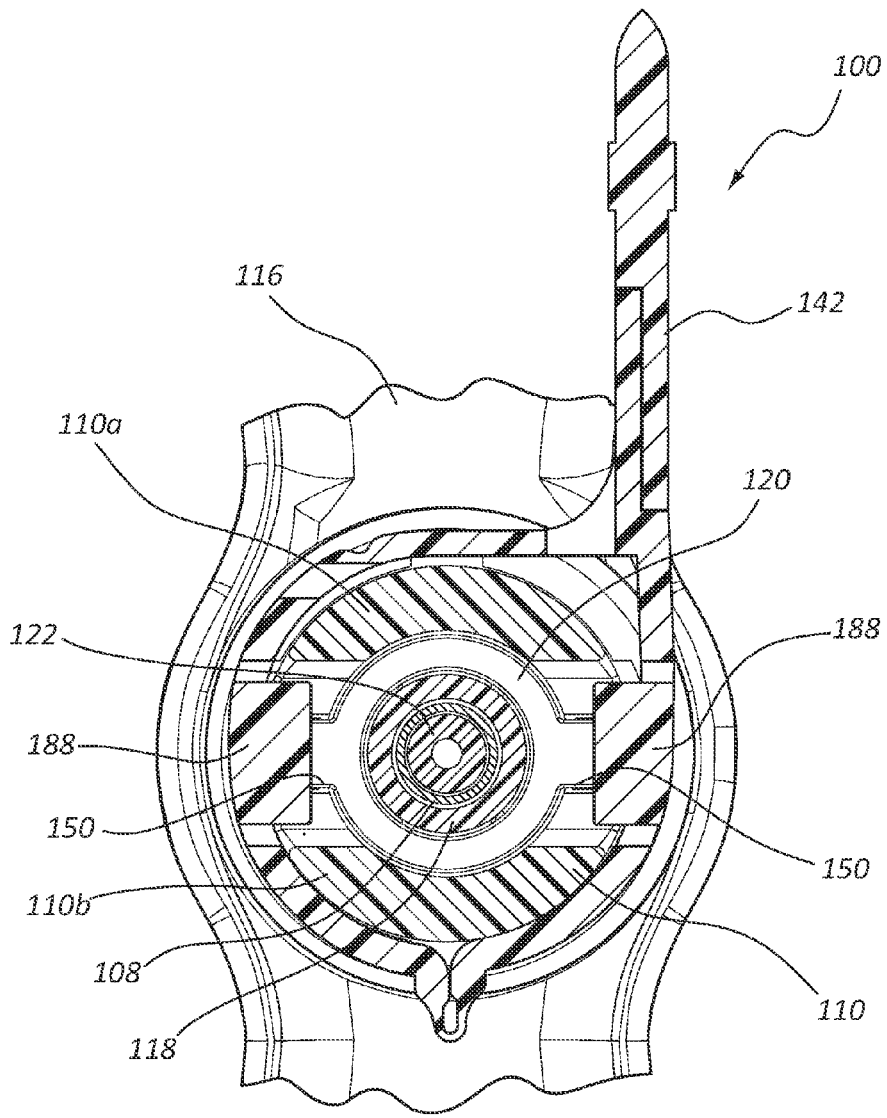
FIGS. 5A and 5B are a longitudinal cross-sectional view and a transverse cross-sectional view, respectively, of a portion of the stent delivery system of FIG. 1.

FIG. 5A provides a transverse cross-sectional view of the stent delivery system 100 of FIG. 1. FIG. 5A illustrates the nested positioning of the trigger safety 142, the outer supports 110, the floater 118, the rigid support tube 108, and the inner member 122.

Figure 5B:
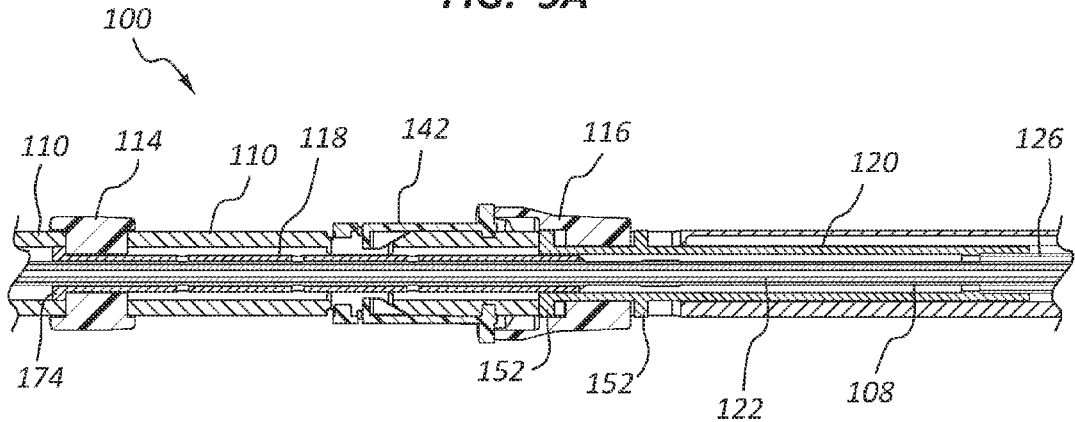

FIG. 5B provides a top longitudinal cross-sectional view of the stent delivery system 100. FIG. 5B illustrates a number of component relationships, in one embodiment. Looking from right to left on the figure, the outer sheath 126 is received into and bonded to an interior surface of the internal connector 120. The internal connector 120 passes through and engages the distal trigger 116. Specifically, the protrusions 152 extending radially outward from the internal connector 120 engage the distal trigger 116. The floater 118 couples together the proximal trigger 114 and the internal connector 120 and the distal trigger 116. In the illustrated embodiment, the distal engagement mechanism 172 (FIG. 4) of the floater 118 engages the internal connector 120 and the proximal engagement connector 174 engages the floater engagement ring 170 (FIG. 4A) of the proximal trigger 114. The rigid support tube 108 extends within the floater 118 and the internal connector 120 and around the inner member 122.

FIG. 6A is a side view and FIG. 6B is a top sectional view illustrating the coupling relationship of the internal connector 120, the distal trigger 116, the floater 118, and the proximal trigger 114. Referring collectively to FIGS. 6A and 6B, the distal trigger 116 couples to the internal connector 120. In the illustrated embodiment, the one or more outwardly extending protrusions 152 on the internal connector 120 mate with the trigger guides 158. As the distal trigger 116 is retracted proximally, toward the handle 106, the distal trigger 116 retracts the internal connector 120 proximally. Thus, retraction of the distal trigger 116 results in retraction of the outer sheath 126 and pod 134 (FIG. 4), which results in at least partial deployment of the stent 10.

The proximal trigger 114 is mechanically coupled to the distal trigger 116 by the floater 118. In the illustrated embodiment, the proximal trigger 114 further includes a floater engagement ring 170 coupled to the inwardly protruding trigger guides 168 (see also FIG. 4). The floater engagement ring 170 engages the proximal engagement mechanism 174 at the proximal end of the floater 118, such that proximal movement of the proximal trigger 114 in turn retracts the floater 118. The distal end of the floater 118 in turn engages the distal trigger 116 and/or the internal connector 120. Accordingly, retraction of the proximal trigger 114 results in retraction of the distal trigger 116 and/or the internal connector 120, which results in at least partial deployment of the stent 10.

FIGS. 7A-7D are cross-sectional views of the stent delivery system 100 at various stages of deployment, illustrating operation of the proximal trigger 114, the floater 118, the distal trigger 116, the internal connector 120, and the outer sheath 126 to deploy a stent 10. FIG. 7A shows the stent delivery system 100 prior to the trigger safety 142 being removed. FIG. 7A-1 provides a close-up view of the pod 134. The trigger safety 142 is engaged around the outer supports 110. The pod 134 is abutting the tip 132 at position $Ppod_1$, fully enclosing the stent 10 in a compressed sheathed configuration. The distal trigger 116 is positioned substantially at or toward the distal end of the one or more trigger guide slots 150 (see FIG. 2) of the outer supports 110 at position $Pd_1$. The proximal trigger 114 is positioned at position $Pp_1$.

FIG. 7B is a side longitudinal cross-sectional view of the stent delivery system 100 of FIG. 1 prior to deployment. FIG. 7B-1 provides a close-up view of the pod 134. The stent 10 is compressed around the pod spacer 130. The pod 134 at the distal end of the outer sheath 126 is positioned completely over the collapsed stent 10 and the pod spacer 130. In other words, the stent 10 is fully sheathed inside the pod 134. The pod 134 is still abutting the tip 132 at position $Ppod_1$, the distal trigger 116 remains at position $Pd_1$. and the proximal trigger 114 remain at position $Pp_1$. The trigger safety 142 is removed (and therefore is not shown in FIGS. 7B-7D), thereby allowing deployment of the stent 10 to occur.

FIG. 7C is a side longitudinal cross-sectional view of the stent delivery system 100 of FIG. 1 with the proximal trigger 114 fully retracted from position $Pp_1$ to position $Pp_2$. FIG. 7C-1 provides a close-up view of the pod 134 positioned within the body lumen 22. Proximal retraction of the proximal trigger 114 results in proximal retraction of the floater 118, which in turn displaces the distal trigger 116 from position $Pd_1$ to position $Pd_2$. As shown, position $Pd_2$ may be substantially proximate to position $Pp_1$. Proximal retraction of the distal trigger 116 results in proximal retraction of the internal connector 120 and the outer sheath 126. As illustrated, proximal retraction of the outer sheath 126 results in at least partial deployment of the stent 10. The pod 134 is shown displaced proximally from position $Ppod_1$ to position $Ppod_2$, away from the tip 132, exposing a portion of the stent 10. The stent 10 is partially deployed and the portion of the stent 10 exposed outside the pod 134 is expanded. When the proximal trigger 114 is fully retracted, a practitioner can more easily reach the distal trigger 116.

FIG. 7D is a side longitudinal cross-sectional view of the stent delivery system of FIG. 1 with the distal trigger 116 fully retracted from position $Pd_1$ to position $Pd_3$. FIG. 7C-1 provides a close-up view of the stent 10 deployed within the body lumen 22. The floater 118 is telescoped into the internal connector 120. The pod 134 is completely retracted, from position $Ppod_1$ to position $Ppod_3$, and fully withdrawn from the stent 10 allowing the stent 10 to fully expand and deploy within the body lumen 22.

As described above, the design and coupling of the floater 118 to the internal connector 120 (and/or distal trigger 116) allow the distal trigger 116 (and internal connector 120) to move proximally relative to the floater 118, thus enabling the two-trigger mechanism of the stent delivery system 100. A two-trigger design allows an elegant, ergonomic mechanism to enable a practitioner to deploy a longer stent (e.g., a stent with a length longer than the finger span of the practitioner. The two-trigger design also allows a two-stage stent deployment process, enabling repositioning of the stent after partial deployment and before complete deployment. A three-trigger design enables deployment of still longer stents, as described below with reference to FIGS. 10, 11A and 11B. Typically, a maximum trigger reach of a hand of a woman over sixty years of age in the fifth percentile is approximately 3.4 inches. Accordingly, the distance between the triggers and/or handle may be no greater than approximately 3.4 inches.

FIGS. 8A-8C are a trigger safety 142 of a stent delivery system, according to one embodiment of the present disclosure. The trigger safety 142 may include an annular body 182 configured to encircle and engage the outer supports 110 (shown in FIG. 5A), and a release tab 184 for opening the body 182 to release the trigger safety. The body 182 may comprise a hinge 186 to allow the body 182 to open and disengage from the outer supports 110. The hinge 186 allows the trigger safety 142 to transition from a closed configuration for engagement of delivery system 100 to an open configuration for releasing from engagement of the delivery system 100. One or more inward protrusions 188 are configured to engage the trigger safety notch 144 (shown in FIG. 4) of the outer supports 110, proximal and adjacent to the distal trigger 116, when the trigger safety is in the closed configuration around the outer supports 110. One or more alignment ribs 189 are configured to engage the trigger guide slot 150 (shown in FIG. 3A) to appropriately align the trigger safety 142. The body 182 of the trigger safety 142, when engaged with the outer supports 110, may abut against the proximal side of the distal trigger 116 and restrict proximal movement of the distal trigger 116. When the distal trigger 116 is unable to move proximally, neither the proximal trigger 114 nor the internal connector 120 and outer sheath 126 can move proximally. In this manner, the trigger safety 142 may guard against inadvertent or accidental deployment of a sheathed stent. In one embodiment, one or more shoulders may protrude radially from the body 182 to provide a larger surface area against which the distal trigger 116 can abut.

The release tab 184 of the trigger safety 142 allows for simple and convenient release of the trigger safety 142 from engagement around the outer supports 110. In the illustrated embodiment, the release tab 184 is a tongue-like projection extending away from the body 182 and oriented substantially at a tangent to the ring-like body 182. The release tab 184 may be coupled to the body 182 by one or more hinged extensions 190. The hinged extensions 190 may include a hinge 192 to allow the hinged extensions 190 and the release tab 184 to rotate away from the body 182. The release tab 184 may engage a projection 194 on the body 182 so as to maintain the body 182 closed position. As shown in FIG. 8C, lifting or pulling the release tab 184 away from the body 182 causes the hinged extensions 190 and the release tab 184 to rotate away from the body 182. As the release tab 184 rotates away from the body 182, the release tab 184 disengages from the projection 194 and allows the body 182 to open. Once the trigger safety 142 is open, it can be removed from the outer supports 110 to allow operation of the trigger assembly 102 (see FIGS. 7A-7D).

Figure 9A:
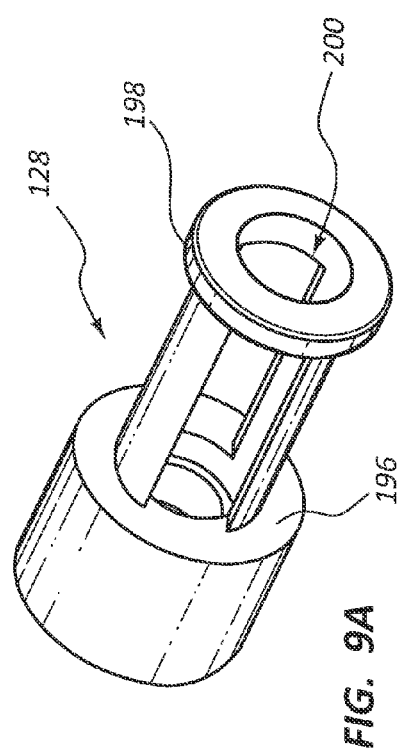
FIGS. 9A and 9B are views of a panchor component of a stent delivery system, according to one embodiment of the present disclosure.
Figure 9B:
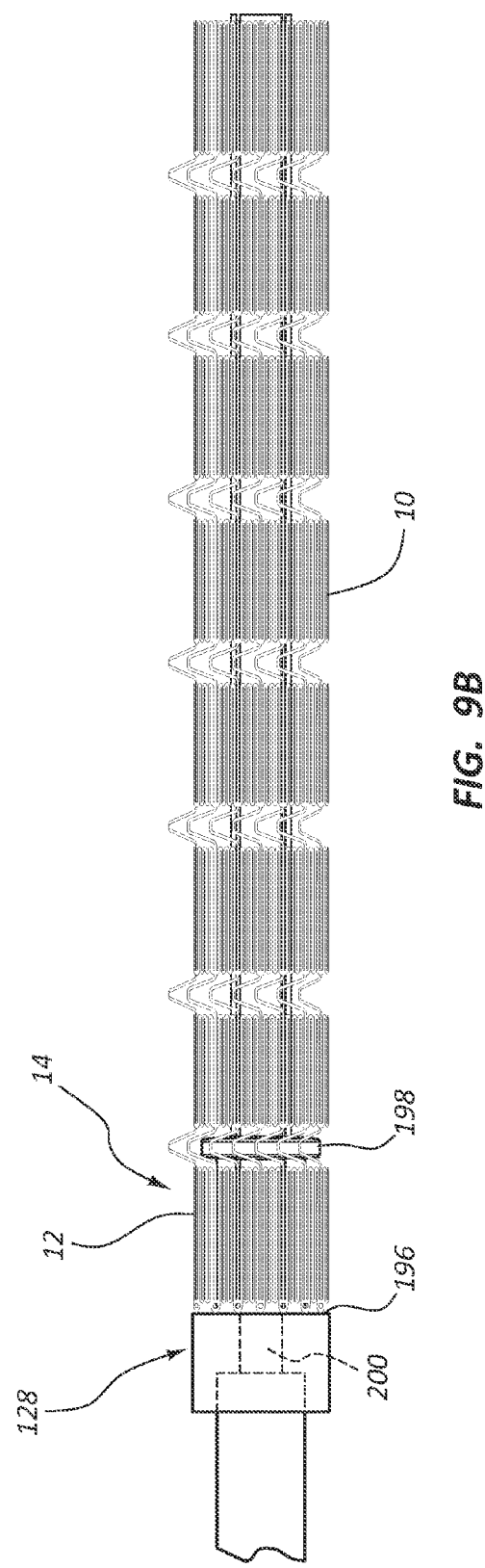

FIG. 9A is a perspective view of a panchor 128 of a stent delivery system, according to one embodiment of the present disclosure. FIG. 9B is a side view of the panchor 128, illustrating how the panchor 128 may function to push (or stop) a stent 10 and to anchor the stent 10. The panchor 128 may be a combination pusher and anchor component configured to limit proximal and distal movement of an implantable device, such as the stent 10, relative to the inner member 122 and/or inner assembly 140. Referring to FIGS. 9A and 9B, collectively, the panchor 128 may include a push surface 196 and an anchor 198. The push surface 196 may be configured to restrict proximal movement of the stent 10 as the outer sheath 126 is pulled proximally over the stent 10 during deployment. The anchor 198 may include a flange at a distal end of the panchor 128. The anchor 198 may be configured to engage the distal ends of one or more of legs 12 of the most proximal annular segment 14 of the stent 10. Engagement of the legs 12 by the anchor 198 of the panchor 128 restricts distal movement of the stent 10, so long as the proximal end of the stent 10 remains sheathed within the pod 134 and compressed around the panchor 128. A channel 200 through the panchor 128 allows the inner member 122 to pass through to the tip 132.

Figure 10:
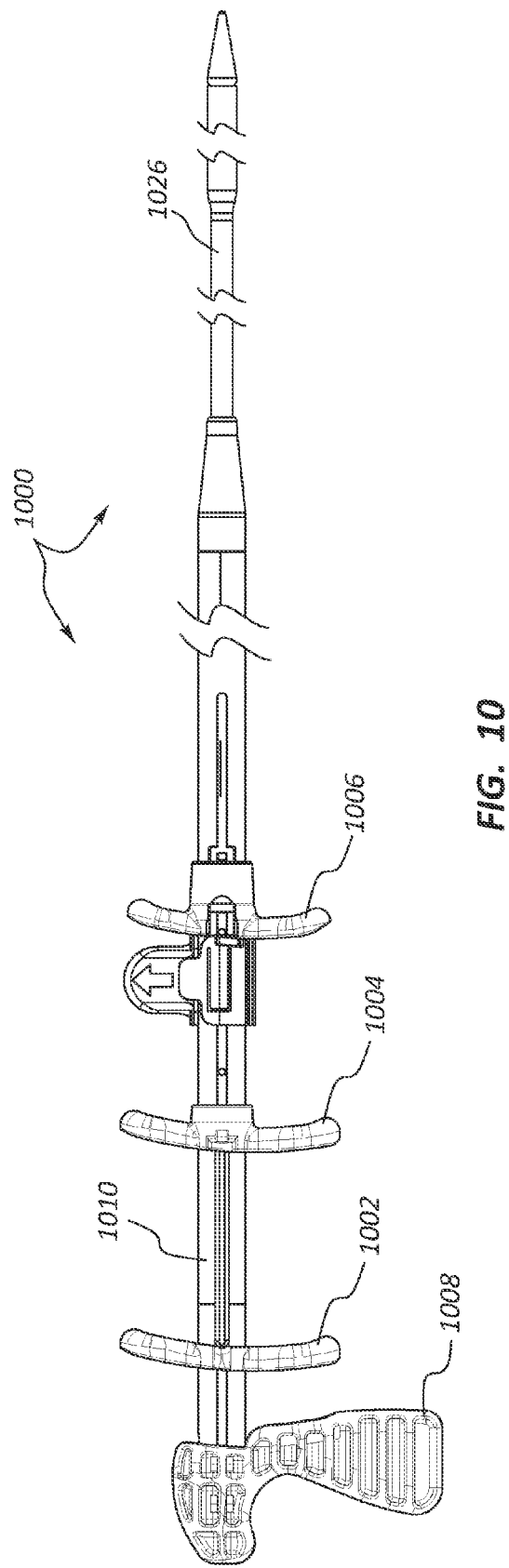
FIG. 10 is a side view of a stent delivery system having three triggers, according to another embodiment of the present disclosure.

FIG. 10 is a side view of a stent delivery system 1000 having three triggers 1002, 1004, 1006 that a practitioner can manipulate to retract an outer sheath 1026 to deploy the stent. Other components of the stent delivery system 1000 may be substantially similar to the components of stent delivery system 100 described above. The three triggers 1002, 1004, 1006 may be operated sequentially, each to partially deploy the stent. The first trigger 1002, may be pulled proximally, toward a handle 1008, to partially deploy the stent. A second trigger 1004 may then be pulled proximally, toward the handle 1008 and the first trigger 1002, to further deploy the stent. Finally, a third trigger 1006 may then be pulled proximally, toward the handle 1008 and the first trigger 1002 and second trigger 1004, to complete deployment of the stent. A trigger safety 1042 may limit proximal movement of the third trigger 1006 (and thereby limiting proximal movement of the first trigger 1002 and second trigger 1004), to restrict deployment of the stent.

The first trigger 1002 may include an annular base configured to encircle the outer supports 1010 and one or more finger holds. The first trigger 1002 couples to the second trigger 1004, such that proximal movement of the first trigger 1002 results in proximal movement of the second trigger 1004. The second trigger 1004 may be substantially similar in structure, function, and/or operation to the proximal trigger 114 of the stent delivery system 100 described above. The third trigger 1006 may be substantially similar in structure, function, and/or operation to the distal trigger 116 described above. Moreover, the coupling and operation of the second trigger 1004 and the third trigger 1006 may be substantially similar to the proximal trigger 114 and distal trigger 116 of the stent delivery system 100, as described above.

FIG. 11A is a side view and FIG. 11B is a top sectional view illustrating the coupling relationship of the first trigger 1002, the second trigger 1004, a floater 1018, an internal connector 120, and the third trigger 1006. The floater 1018 and internal connector 1020 may be substantially similar in structure, function, and/or operation to the floater 118 and internal connector 120 of stent delivery system 100 of FIG. 1, described above. The coupling and operation of the second trigger 1004, the floater 1018, the internal connector 1020, and the third trigger 1006 may be substantially similar to the corresponding components of the stent delivery system 100, as described above with reference to FIGS. 6A and 6B.

Referring collectively to FIGS. 11A and 11B, the third trigger 1006 couples to the internal connector 1020. In the illustrated embodiment, one or more outwardly extending protrusions 1052 on the internal connector 1020 mate with trigger guides on the third trigger 1006. As the third trigger 1006 is retracted proximally, toward the handle 1008, the third trigger 1006 retracts the internal connector 1020 proximally. Thus, retraction of the third trigger 1006 results in retraction of the outer sheath and pod, which results in at least partial deployment of a stent sheathed within the pod.

The second trigger 1004 is mechanically coupled to the third trigger 1006 by the floater 1018. In the illustrated embodiment, the floater 1018 engages a floater engagement ring (coupled to inwardly protruding trigger guides) of the second trigger 1004. The floater engagement ring engages the proximal end of the floater 1018 such that proximal movement of the second trigger 1004 in turn retracts the floater 1018. The distal end of the floater in turn engages the third trigger 1006 and/or the internal connector 1020. Accordingly, retraction of the second trigger 1004 results in retraction of the third trigger 1006 and/or the internal connector 1020, which in turn retracts the outer sheath 1026 and at least partially deploys a sheathed stent.

The first trigger 1002 includes one or more barbed engagement arms 1012 that may extend distally from the base of the first trigger 1002 to engage the second trigger 1004. Barbs 1014 at the distal end of the engagement arms 1012 may engage a base of the second trigger 1004 as the first trigger 1002 moves proximally, while allowing distal movement of the of the first trigger 1002 relative to the second trigger 1002. Stated differently, the barbed engagement arms 1002 allow the second trigger 1004 to move proximally relative to the first trigger 1002, such that the second trigger 1004 can be operated and retracted toward the first trigger 1002, even after the first trigger 1002 has been retracted.

As can be appreciated, other embodiments are possible in which additional triggers, beyond three, are coupled together in a similar manner as described herein.

The present disclosure may be embodied in other specific forms without departing from its spirit or essential characteristics. The described embodiments are to be considered in all respects only as illustrative and not restrictive. As can be appreciated by those having skill in the art, many changes may be made to the details of the above-described embodiments without departing from the underlying principles of the invention. The scope of the invention is, therefore, indicated by the appended claims rather than by the foregoing description. All changes which come within the meaning and range of equivalency of the claims are to be embraced within their scope.

What is claimed is:

1. A delivery system for deploying an implantable device within a lumen internal to a body of a patient, the delivery system comprising:
   an inner member having a proximal end coupled to a handle of the delivery system and extending toward a distal end of the delivery system to couple to the implantable device;
   an outer sheath having a proximal end and a distal end, the outer sheath surrounding a distal portion of the inner member and configured to retain the implantable device sheathed near the distal end of the outer sheath until deployment, wherein the outer sheath is slidably moveable relative to the inner member such that proximal movement of the outer sheath relative to the inner member deploys the implantable device;
   a trigger assembly coupled to the outer sheath comprising:
      an internal connector coupled to the outer sheath and including a floater engagement surface;
      a distal trigger configured to engage the internal connector to retract the internal connector as the distal trigger is retracted proximally;
      a floater having a distal end and a proximal end, the distal end configured to engage a floater engagement surface of the internal connector to retract the internal connector as the floater is retracted proximally; and
      a proximal trigger configured to engage the floater to retract the floater as the proximal trigger is retracted proximally,
   wherein the distal trigger and the proximal trigger are configured to be serially retracted to provide staged release of the implantable device such that retracting the proximal trigger moves the distal trigger and the outer sheath proximally and longitudinally relative to the inner member from a first position to a second position to partially deploy the implantable device, and wherein subsequent retraction of the distal trigger moves the outer sheath proximally and longitudinally relative to the inner member from the second position to a third position to fully deploy the implantable device.

2. The delivery system of claim 1, wherein the internal connector has a tubular shape configured to surround a portion of the inner member, a distal end of the internal connector coupled to the proximal end of the outer sheath, wherein the internal connector is slidably moveable relative to the inner member and movement of the internal connector relative to the inner member results in movement of the outer sheath relative to the inner member;
   wherein the distal trigger is configured to engage a proximal end of the internal connector as the distal trigger is retracted proximally toward the handle of the delivery system, wherein proximal movement of the distal trigger results in proximal movement of the internal connector and the outer sheath relative to the inner member;
wherein the floater has a tubular shape configured to surround a portion of the inner member, wherein the floater is slidably moveable relative to the inner member and proximal movement of the floater relative to the inner member results in proximal movement of the floater, the distal trigger, and the outer sheath relative to the inner member; and
wherein the proximal trigger is configured to engage a proximal end of the floater as the proximal trigger is retracted proximally toward the handle of the delivery system, wherein proximal movement of the proximal trigger results in proximal movement of each of the floater, the distal trigger, the internal connector, and the outer sheath relative to the inner member.

3. The delivery system of claim 2, wherein the implantable device is a stent, and wherein the inner member is configured to be disposed through the stent to couple to a conical tip,
wherein the stent is configured to be compressed and sheathed within a distal portion of the outer sheath.

4. The delivery system of claim 3, further comprising a panchor configured to couple to a proximal portion of the stent in a sheathed configuration, wherein the panchor is a combination pusher and anchor component configured to limit proximal and distal movement of the stent relative to the inner member.

5. The delivery system of claim 4,
wherein the stent comprises a scaffolding structure formed of a plurality of rows of struts or legs oriented about an outer circumference of the stent and connected by a plurality of connectors extending longitudinally with a longitudinal axis of the stent,
wherein the panchor comprises a push surface and an anchor, the push surface configured to restrict proximal movement of the stent relative to the inner member as the outer sheath is retracted proximally over the stent during deployment, the anchor including a flange configured to engage distal ends of one or more legs of a most proximal row of the plurality of rows of the stent and thereby restrict distal movement of the stent relative to the inner member.

6. The delivery system of claim 4, wherein the panchor is configured to push against the stent as a force in a proximal direction is exerted on the stent and is configured to anchor the stent as a force in a distal direction is exerted on the stent.

7. The delivery system of claim 1, wherein the floater is configured to telescope into the internal connector to allow the internal connector to move proximally relative to the floater and allow proximal movement of the distal trigger relative to the proximal trigger, to thereby enable serial retraction of the proximal trigger and then the distal trigger.

8. The delivery system of claim 7, wherein the internal connector comprises a floater engagement surface disposed at a proximal end of each of a pair of floater engagement channels, wherein the floater includes a pair of barbed prongs configured to slide distally within the floater engagement channels to enable the floater to telescope into the internal connector and to engage the floater engagement surface as the barbed prongs move proximally to the proximal end of the floater engagement channels, such that proximal movement of the floater results in proximal movement of the internal connector.

9. The delivery system of claim 1, further comprising a pod disposed at a distal end of the outer sheath, wherein the pod is configured to enclose the implantable device in a sheathed configuration until deployment, and wherein proximal movement of the outer sheath relative to the inner member results in proximal movement of the pod relative to the inner member to deploy the implantable device.

10. The delivery system of claim 1, further comprising one or more outer supports extending distally from the handle and configured to provide a support structure supporting the distal trigger and proximal trigger and along which the distal trigger and proximal trigger can slide as they are retracted to deploy the implantable device.

11. The delivery system of claim 10, wherein the one or more outer supports comprise an upper outer support and a lower outer support configured to mate together to form a tubular shaped housing around a portion of the proximal end of the outer sheath, the internal connector, the floater, and a proximal portion of the inner member.

12. The delivery system of claim 10, wherein the one or more outer supports are configured to form a trigger guide slot extending longitudinally along a length of the outer supports to provide a track or guide for the distal trigger and the proximal trigger as they move proximally relative to the one or more outer supports.

13. The delivery system of claim 10, wherein the outer supports provide one or more trigger safety notches configured to be engaged by a trigger safety to limit proximal movement of the distal trigger and the proximal trigger and thereby inhibit deployment of the implantable device.

14. The delivery system of claim 1, further comprising a trigger safety configured to engage the delivery system at one of a first trigger safety notch and a second trigger safety notch to restrict proximal movement of the distal trigger and outer sheath relative to the inner member.

15. The delivery system of claim 14, wherein the trigger safety is configured to engage one or more outer supports of the delivery system and configured to engage the internal connector to limit proximal movement of the internal connector relative to the one or more outer supports and inner member.

16. The delivery system of claim 14, wherein the trigger safety comprises:
a body having a closed configuration forming an annular shape configured to encircle and engage outer supports of the delivery system, the body having a hinge configured to allow the body to open and disengage from the outer supports of the delivery system, the body comprising:
an alignment rib disposed on an inner surface of the body and configured to engage protrusions on an internal connector and restrict proximal movement of the internal connector relative to the trigger safety; and
an inward protrusion extending inward from an inner surface of the body to engage a notch formed in the outer supports and configured to restrict proximal movement of the trigger safety relative to the outer supports; and
a release tab configured to open the body to release the trigger safety.

17. The delivery system of claim 1, further comprising a rigid support tube coupled to the handle and positioned around a proximal portion of the inner member, the rigid support tube configured to provide a rigid internal structure to support the distal trigger and the proximal trigger during proximal retraction.

18. The delivery system of claim 1, further comprising a third trigger positioned proximal to the proximal trigger and coupled to the proximal trigger, wherein the third trigger, the proximal trigger, and the distal trigger are configured to be serially retracted to provide staged release of the implantable device such that retracting the third trigger moves the proximal trigger, the distal trigger and the outer sheath proximally and longitudinally relative to the inner member from the first position to the second position to partially deploy the implantable device, and wherein subsequent retraction of the proximal trigger moves the distal trigger and the outer sheath proximally and longitudinally relative to the inner member from the second position to the third position to further partially deploy the implantable device, and wherein subsequent retraction of the distal trigger moves the outer sheath proximally and longitudinally relative to the inner member from the third position to a fourth position to fully deploy the implantable device.

19. The delivery system of claim 1, wherein the implantable device comprises a stent, and the delivery system further comprises:
an inner assembly disposed around a portion of the inner member, the inner assembly comprising a middle sheath configured around the inner member to provide additional structural support for the inner member against buckling, crimping, and undesired bending and collapse of the inner member, and the inner assembly further comprising a panchor disposed at the distal end of the middle sheath, wherein the panchor is a combination pusher and anchor configured to couple to a proximal portion of the stent to limit proximal and distal movement of the stent relative to the inner assembly.

20. The delivery system of claim 19, wherein the stent comprises a scaffolding structure formed of a plurality of rows of struts or legs oriented about an outer circumference of the stent and connected by a plurality of connectors extending longitudinally with a longitudinal axis of the stent, wherein the stent is configured to be compressed and sheathed within a distal portion of the outer sheath.

21. The delivery system of claim 20, wherein the panchor comprises a push surface and an anchor, the push surface configured to restrict proximal movement of the stent as the outer sheath is retracted proximally over the stent during deployment, the anchor including a flange configured to engage the distal ends of one or more legs of an annular segment of the stent and thereby restrict distal movement of the stent.

22. The delivery system of claim 19, wherein the floater comprises:
a tubular shape configured to surround a portion of the inner assembly;
a distal end; and
a proximal end,
wherein the distal end is configured to couple to the distal trigger as the floater is retracted proximally toward the handle of the delivery device,
wherein the proximal trigger is configured to engage the floater as the trigger is retracted proximally toward the handle,
wherein the floater is slidably moveable relative to the inner assembly and proximal movement of the floater relative to the inner assembly results in proximal movement of the floater, the distal trigger, and the outer sheath relative to the inner assembly and inner member, and
wherein the floater is configured to allow the distal trigger to be retracted proximally relative to the proximal trigger for serial retraction of the proximal trigger and the distal trigger.

23. The delivery system of claim 19, wherein the internal connector comprises:
a tubular shape configured to surround a portion of the inner assembly;
a distal end; and
a proximal end,
wherein the distal end is coupled to the proximal end of the outer sheath and the proximal end is configured to be engaged by the distal trigger as the distal trigger is retracted proximally toward the handle of the delivery device, and
wherein the internal connector is slidably moveable relative to the inner assembly and movement of the internal connector relative to the inner assembly results in movement of the outer sheath relative to the inner assembly and inner member.

24. The delivery system of claim 23, further comprising a trigger safety configured to engage the internal connector to restrict proximal movement of the distal trigger and outer sheath relative to the inner assembly and inner member.

25. The delivery system of claim 19, wherein the inner assembly further comprises a rigid support tube coupled to the handle of the delivery device and positioned around a proximal portion of the inner member, the rigid support tube configured to provide a rigid internal structure to support the proximal trigger and the distal trigger during retraction to deploy the stent.

26. A method of deploying a stent within a target lumen of a body of a patient, the method comprising:
obtaining a stent delivery system comprising a stent and a stent delivery device with the stent fully sheathed in a sheathed configuration within a distal portion of an outer sheath of the stent delivery system, the delivery system including a panchor disposed adjacent the distal end of the stent delivery system, wherein the panchor is a combination pusher and anchor configured to couple to a proximal portion of the stent to limit proximal and distal movement of the stent along with the outer sheath during deployment;
positioning a distal portion of the outer sheath, including the sheathed stent, within the target lumen;
retracting a proximal trigger to partially deploy the stent within the target lumen, wherein the proximal trigger is coupled to a floater to retract the floater as the proximal trigger is retracted proximally, the floater configured to engage a floater engagement surface of an internal connector to retract the internal connector as the floater is retracted proximally, the internal connector coupled to the outer sheath to retract the outer sheath as the internal connector is retracted proximally, the internal connector coupled to a distal trigger such that movement of the proximal trigger results in proximal movement of each of the distal trigger and the outer sheath relative to the stent to unsheathe a portion of the stent;
retracting the distal trigger to further retract the internal connector to further retract the outer sheath to fully deploy the stent within the target lumen, wherein proximal movement of the distal trigger results in proximal movement of the outer sheath relative to the inner member; and
withdrawing the distal portion of the outer sheath from the target lumen.

27. A delivery system for deploying an implantable device within a lumen internal to a body of a patient, the delivery system comprising:
an inner member having a proximal end coupled to a handle of the delivery system and extending toward a distal end of the delivery system to couple to the implantable device;

an outer sheath having a proximal end and a distal end, the outer sheath surrounding a distal portion of the inner member and configured to retain the implantable device sheathed near the distal end of the outer sheath until deployment, wherein the outer sheath is slidably moveable relative to the inner member such that proximal movement of the outer sheath relative to the inner member deploys the implantable device;

an internal connector having a tubular shape configured to surround a portion of the inner member and having a distal end and a proximal end and a floater engagement surface near the proximal end, the distal end coupled to the proximal end of the outer sheath, wherein the internal connector is slidably moveable relative to the inner member and movement of the internal connector relative to the inner member results in movement of the outer sheath relative to the inner member;

a distal trigger configured to engage a proximal end of the internal connector as the distal trigger is retracted proximally toward the handle of the delivery system, wherein proximal movement of the trigger results in proximal movement of the internal connector and the outer sheath relative to the inner member;

a floater having a tubular shape configured to surround a portion of the inner member and having a distal and a proximal end, the distal end configured to engage the floater engagement surface of the internal connector to retract the internal connector as the floater is retracted proximally, wherein the floater is slidably moveable relative to the inner member and proximal movement of the floater relative to the inner member results in proximal movement of the floater, the distal trigger, and the outer sheath relative to the inner member; and a proximal trigger configured to engage a proximal end of the floater as the proximal trigger is retracted proximally toward the handle of the delivery system, wherein proximal movement of the proximal trigger results in proximal movement of each of the floater, the distal trigger, the internal connector, and the outer sheath relative to the inner member, wherein the distal trigger and the proximal trigger are configured to be serially retracted to provide staged release of the implantable device such that retracting the proximal trigger moves the distal trigger and the outer sheath proximally and longitudinally relative to the inner member from a first position to a second position to partially deploy the implantable device, and wherein subsequent retraction of the distal trigger moves the outer sheath proximally and longitudinally relative to the inner member from the second position to a third position to fully deploy the implantable device.

* * * * *